US006284727B1

(12) United States Patent
Kim et al.

(10) Patent No.: US 6,284,727 B1
(45) Date of Patent: Sep. 4, 2001

(54) PROLONGED DELIVERY OF PEPTIDES

(75) Inventors: Yesook Kim; William J. Lambert; Hong Qi; Robert A Gelfand; Kieran F. Geoghegan; Dennis E. Danley, all of New York, NY (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 08/472,349

(22) Filed: Jun. 7, 1995

Related U.S. Application Data

(63) Continuation of application No. 08/181,655, filed on Jan. 25, 1994, now abandoned, which is a continuation-in-part of application No. 08/044,133, filed on Apr. 7, 1993, now abandoned.

(51) Int. Cl.⁷ ..................................................... A61K 38/00
(52) U.S. Cl. ............................................. 514/12; 530/324
(58) Field of Search ................................ 514/12; 530/324

(56) References Cited

U.S. PATENT DOCUMENTS

| | | | |
|---|---|---|---|
| 4,654,324 | * 3/1987 | Chance et al. | 514/12 |
| 4,857,505 | * 8/1989 | Ardent | 514/2 |
| 4,985,404 | * 1/1991 | Mitchell | 514/6 |
| 5,118,666 | * 6/1992 | Habener | 514/12 |
| 5,120,712 | * 6/1992 | Habener | 514/12 |
| 5,175,145 | * 12/1992 | Cooper | 514/4 |
| 5,424,286 | 6/1995 | Eng | 514/2 |
| 5,545,618 | 8/1996 | Buckley et al. | 514/2 |
| 5,574,008 | 11/1996 | Johnson et al. | 514/12 |
| 5,614,492 | 3/1997 | Habener | 514/12 |
| 5,631,224 | 5/1997 | Efendic | 514/12 |

FOREIGN PATENT DOCUMENTS

| | | | |
|---|---|---|---|
| 19530865 A1 | 2/1997 | (DE) . | |
| 0 177 478 | 4/1986 | (EP) . | |
| 0 343 696 A2 | 11/1989 | (EP) . | |
| 0 442 671 A2 | 8/1991 | (EP) . | |
| 0 473 268 A3 | 3/1992 | (EP) . | |
| 0 526 862 A1 | 2/1993 | (EP) . | |
| 0 619 322 A2 | 10/1994 | (EP) . | |
| 0 658 568 A1 | 6/1995 | (EP) . | |
| 0 733 644 A1 | 9/1996 | (EP) . | |
| 2 732 894 | 10/1996 | (FR) . | |
| 06941 | * 11/1987 | (WO) | C07K/7/10 |
| WO 88/07366 | 10/1988 | (WO) . | |
| WO 90/02835 | 3/1990 | (WO) . | |
| 11296 | * 10/1990 | (WO) | C07K/7/10 |
| 11457 | * 8/1991 | (WO) | C07K/7/34 |
| WO 93/18785 | 9/1993 | (WO) . | |
| WO 93/18786 | 9/1993 | (WO) . | |
| WO 93/19175 | 9/1993 | (WO) . | |
| WO 93/25579 | 12/1993 | (WO) . | |
| WO 95/05848 | 3/1995 | (WO) . | |
| WO 95/07098 | 3/1995 | (WO) . | |
| WO 95/17510 | 6/1995 | (WO) . | |
| WO 95/31214 | 11/1995 | (WO) . | |
| WO 96/20005 | 4/1996 | (WO) . | |

OTHER PUBLICATIONS

Kreymann et al, Laneef Dec. 5, 1987 p. 1300.*
Conn's Current Therapy p. 483. (1989).*
Remington's Pharmaceutical Sciences, 16th ed. p. 1555, 1467, 1453, 1451, 1450, 1448, CH 91, 1980.*
Cross et al., "Subcutaneous Absorption Kinetics And Local Tissue Distribution Of Interferon And Other Solutes," J. Pharm. Pharmacol., 1993, 45, pp. 606–609.
Hirano et al., "Studies on the Absorption of Practically Water–Insolable Drugs Following Injection VIII: Comparison of the Subcutaneous Absorption Rates From Aqueous Suspensions in the Mouse, Rat and Rabbit," J. Pharm. Sci., 1993, 72(6), pp. 608–612.
Nara et al., "A New Method for Assessment of Drug Absorption From Muscle: Application of a Local Perfusion System," J. Pharm. Pharmacol, 1991, 43, pp. 272–274.
Dickert et al., "Absorption of NPH–Insulin from Subcutaneous Tissue: A Methodological Study in Pigs," ACTA Pharmacol et Toxicol, 1982, 51, pp. 30–37.
Supersaxo et al., "Effects of Molecular Weight on the Lymphatic Absorption of Water–Soluble Compounds Following Subcutanous Administration," Pharmaceutical Research, 1990, 7(2), pp. 167–169.
Mosjov, "Structural Requirements for Biological Activity of Glucagon–Like Peptide–1, " Int. J. Peptide Protein Res., 1992, 40, pp. 333–343.
Suzuki et al., "Comparison of the Effects of Various C–Terminal and N–Terminal Fragment Peptide of Glucogen–Like Peptide–1 or Insulin and Glucagon Release from the Isolated Perfused Rat Pancreas," Endocrinology, 1989, 125(6), pp. 3109–3113.
Krówczyński, Leszek, "Technologia postaci leków (Technology of the drug forms)", Państwowy Zaklad Wydawnictw Lekarskich Warszawa, 1969, pp. 220, 463–464, 490, 502.
Gennaro, Alfonso R., Chapter 23 in Remington's Pharmaceutical Sciences, 16th edition, A. Osol Editor, Mack Publishing Company, Easton, PA, 1980, pp. 343–363.
Gill, I. J. et al., "Cyclodextrins as protection agents against enhancer damage in nasal delivery systems II. Effect on in vivo absorption of insulin and histopathology of nasal membrane," *European Journal of Pharmaceutical Sciences* 1:237–248, Jun. 1994.
Hendrick, G.K. et al., "Glucagon–like Peptide–I–(7–37) Suppresses Hyperglycemia in Rats," *Metabolism* 42(1):1–6, Jan. 1993.

(List continued on next page.)

Primary Examiner—Sheela Huff
(74) Attorney, Agent, or Firm—Sterne, Kessler, Goldstein & Fox P.L.L.C.

(57) ABSTRACT

There are disclosed methods for the treatment of non-insulin dependent diabetes mellitus in a mammal comprising the prolonged administration of GLP-1 (7–37), and related peptides. Also disclosed are compositions to prolong the administration of the peptides.

37 Claims, 10 Drawing Sheets

OTHER PUBLICATIONS

Holst, J.J. et al., "Truncated glucago–like peptide I, an insulin–releasing hormone for the distal gut," *FEBS Letters* 211(2):169–174, Jan. 1987.

Remington'Pharmaceutical Sciences, 16th ed. pp. 1555, 1467, 1453, 1451, 1450, 1448, Ch. 91, 1980.*

Cross et al., "Subcutaneous Absorption Kinetics and Local Tissue Distribution of Interferon and other Soluter," J. Pharm. Pharmacol., 1993, 45, pp. 606–609;.

Hirano et al., "Studies on the Absorption of Practically Water–Insoluble Drugs following Injection VIII: Comparison of the Subcutaneous Absorption Rates from Aqueous Suspensions in the Mouse, Rat, and Rabbit," J. Pharm. Sci., 1993, 72(6), pp. 608–612;.

Nara et al., "A New Method for Assessment of Drug Absorption from Muscle: Application of a Local Perfusion System," J. Pharm. Pharmacol, 1991, 43, pp. 272–274;.

Dickert et al., "Absorption of NPH–Insulin from Subcutaneous Tissue: A Methodological Study in Pigs," Acta Pharmacol et Toxicol, 1982, 51, pp. 30–37;.

Supersaxo et al., "Effects of Molecular Weight on the Lymphatic Absorption of Water–Soluble Compounds following Subcutaneoud Administration," Pharmaceutical Research, 1990, 7(2), pp. 167–169;.

Mosjov, "Structural requiremtns for Biological Activity of Glucagon–like Peptide–1," Int. J. Peptide Protein Res., 1992, 40, pp. 333–343;.

Suzuki et al., "Comparison of the Effects of various C–Terminal and N–Terminal Fragment Peptide of Glucogen–like Peptide–1 or Insulin and Glucagon Release from the Isolated Perfused Rat Pancreas," endocrinology, 1989, 125(6), pp. 3109–3113.

* cited by examiner

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 37 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
      (A) ORGANISM: N/A
      (B) STRAIN: N/A
      (C) INDIVIDUAL ISOLATE: N/A
      (E) HAPLOTYPE: N/A
      (H) CELL LINE: N/A (vii) IMMEDIATE SOURCE:
      (A) LIBRARY: N/A
      (B) CLONE: N/A (viii) POSITION IN GENOME:
      (A) CHROMOSOME/SEGMENT: N/A
      (B) MAP POSITION: N/A
      (C) UNITS: N/A (xi) SEQUENCE DESCRIPTION: SEQ ID NO:1:

```
His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Gly
        35
```

(2) INFORMATION FOR SEQ ID NO:2:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: N/A
        (B) STRAIN: N/A
        (C) INDIVIDUAL ISOLATE: N/A
        (E) HAPLOTYPE: N/A
        (H) CELL LINE: N/A (vii) IMMEDIATE SOURCE:
        (A) LIBRARY: N/A
        (B) CLONE: N/A (viii) POSITION IN GENOME:
        (A) CHROMOSOME/SEGMENT: N/A
        (B) MAP POSITION: N/A
        (C) UNITS: N/A (xi) SEQUENCE DESCRIPTION: SEQ ID NO:2:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: N/A
        (B) STRAIN: N/A
        (C) INDIVIDUAL ISOLATE: N/A
        (E) HAPLOTYPE: N/A
        (H) CELL LINE: N/A (vii) IMMEDIATE SOURCE:
        (A) LIBRARY: N/A
        (B) CLONE: N/A (viii) POSITION IN GENOME:
        (A) CHROMOSOME/SEGMENT: N/A
        (B) MAP POSITION: N/A
        (C) UNITS: N/A (xi) SEQUENCE DESCRIPTION: SEQ ID NO:3:

His Ala Glu Gly Thr Phe Thr Ser Asp Val Ser Ser Tyr Leu Glu Gly
1               5                   10                  15

```
Gln Ala Ala Lys Glu Phe Ile Ala Trp Leu Val Lys Gly Arg
        20                  25                  30
```

(2) INFORMATION FOR SEQ ID NO:4:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: N/A
        (B) STRAIN: N/A
        (C) INDIVIDUAL ISOLATE: N/A
        (E) HAPLOTYPE: N/A
        (H) CELL LINE: N/A (vii) IMMEDIATE SOURCE:
        (A) LIBRARY: N/A
        (B) CLONE: N/A (viii) POSITION IN GENOME:
        (A) CHROMOSOME/SEGMENT: N/A
        (B) MAP POSITION: N/A (xi) SEQUENCE DESCRIPTION: SEQ ID NO:4:

```
His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly
        20                  25
```

(2) INFORMATION FOR SEQ ID NO:5:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: N/A
        (B) STRAIN: N/A
        (C) INDIVIDUAL ISOLATE: N/A
        (E) HAPLOTYPE: N/A
        (H) CELL LINE: N/A (vii) IMMEDIATE SOURCE:
        (A) LIBRARY: N/A
        (B) CLONE: N/A (viii) POSITION IN GENOME:
        (A) CHROMOSOME/SEGMENT: N/A
        (B) MAP POSITION: N/A (xi) SEQUENCE DESCRIPTION: SEQ ID NO:5:

```
His Ala Glu Gly Thr Phe Thr Ser Asp Val Ser Ser Tyr Leu Glu Gly
1               5                   10                  15
```

```
Gln Ala Ala Lys Glu Phe Ile Ala Trp Leu Val Lys
            20                  25
```

(2) INFORMATION FOR SEQ ID NO:6:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: N/A
        (B) STRAIN: N/A
        (C) INDIVIDUAL ISOLATE: N/A
        (E) HAPLOTYPE: N/A
        (H) CELL LINE: N/A (vii) IMMEDIATE SOURCE:
        (A) LIBRARY: N/A
        (B) CLONE: N/A (viii) POSITION IN GENOME:
        (A) CHROMOSOME/SEGMENT: N/A
        (B) MAP POSITION: N/A (xi) SEQUENCE DESCRIPTION: SEQ ID NO:6:

```
His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
        35
```

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: N/A
        (B) STRAIN: N/A
        (C) INDIVIDUAL ISOLATE: N/A
        (E) HAPLOTYPE: N/A
        (H) CELL LINE: N/A (vii) IMMEDIATE SOURCE:
        (A) LIBRARY: N/A
        (B) CLONE: N/A (viii) POSITION IN GENOME:
        (A) CHROMOSOME/SEGMENT: N/A
        (B) MAP POSITION: N/A -continued (xi) SEQUENCE DESCRIPTION: SEQ ID NO:7:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val
                20                  25

PROLONGED DELIVERY OF PEPTIDES

This application is a continuation of application Ser. No. 08/181,655, filed Jan. 25, 1994, now abandoned, which is a continuation-in-part of application Ser. No. 08/044,133, filed Apr. 7, 1993, now abandoned.

BACKGROUND OF THE INVENTION

The present invention relates to compositions and methods for the treatment of Diabetes Mellitus. More specifically, the present invention relates to compositions to prolong the administration of glucagon-like peptide 1 (GLP-1), and derivatives thereof. These compositions are useful in treatment of Non-Insulin Dependent Diabetes Mellitus (NIDDM).

The amino acid sequence of GLP-1 is known as:
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1)

GLP-1 is disclosed by Lopez, L. C., et al., P.N.A.S., USA 80: 5485–5489 (1983); Bell, G. I., et al., Nature 302: 716–718 (1983); Heinrich, G. et al., Endocrinol. 115: 2176–2181 (1984) and Ghiglione, M., et al., Diabetologia 27: 599–600 (1984).

During processing in the pancreas and intestine, GLP-1 is converted to a 31 amino acid peptide having amino acids 7–37 of GLP-1, hereinafter this peptide is referred to as GLP-1 (7–37).

This peptide has been shown to have insulinotropic activity, that is, it is able to stimulate, or cause to be stimulated, the synthesis or expression of the hormone insulin. Because of this insulinotropic activity, GLP-1 (7–37) is alternatively referred to as insulinotropin.

GLP-1 (7–37) has the following amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2).

GLP-1 (7–37), certain derivatives thereof and the use thereof to treat Diabetes mellitus in a mammal are disclosed in U.S. Pat. Nos. 5,118,666 ('666 patent) and 5,120,712 ('712 patent), the disclosures of these patents being incorporated herein by reference. The derivatives of GLP-1 (7–37) disclosed in the '666 and '712 patents include polypeptides which contain or lack one or more amino acids that may not be present in the naturally occurring sequence. Further derivatives of GLP-1 (7–37) disclosed in the '666 and '712 patents include certain C-terminal salts, esters and amides where the salts and esters are defined as OM where M is a pharmaceutically acceptable cation or a lower ($C_1$–$C_6$) branched or unbranched alkyl group and the amides are defined as —$NR^2R^3$ where $R^2$ and $R^3$ are the same or different and are selected from the group consisting of hydrogen and a lower ($C_1$–$C_6$) branched or unbranched alkyl group.

Certain other polypeptides, alternatively referred to as truncated GLP-1 or truncated insulinotropin, having insulinotropic activity and the derivatives thereof are disclosed in PCT/US 89/01121 (WO 90/11296). Those polypeptides, referred to therein as GLP-1 (7–36), GLP-1 (7–35) and GLP-1 (7–34) have the following amino acid sequences, respectively.
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4); and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5);

Derivatives of the polypeptides disclosed in PCT/US89/01121 include polypeptides having inconsequential amino acid substitutions, or additional amino acids to enhance coupling to carrier protein or to enhance the insulinotropic effect thereof. Further derivatives of insulinotropin disclosed in PCT/US89/01121 include certain C-terminal salts, esters and amides where the salts and esters are defined as OM where M is a pharmaceutically acceptable cation or a lower branched or unbranched alkyl group and the amides are defined as —$NR^2R^3$ where $R^2$ and $R^3$ are the same or different and are selected from the group consisting of hydrogen and a lower branched or unbranched alkyl group.

SUMMARY OF THE INVENTION

Figure 1:
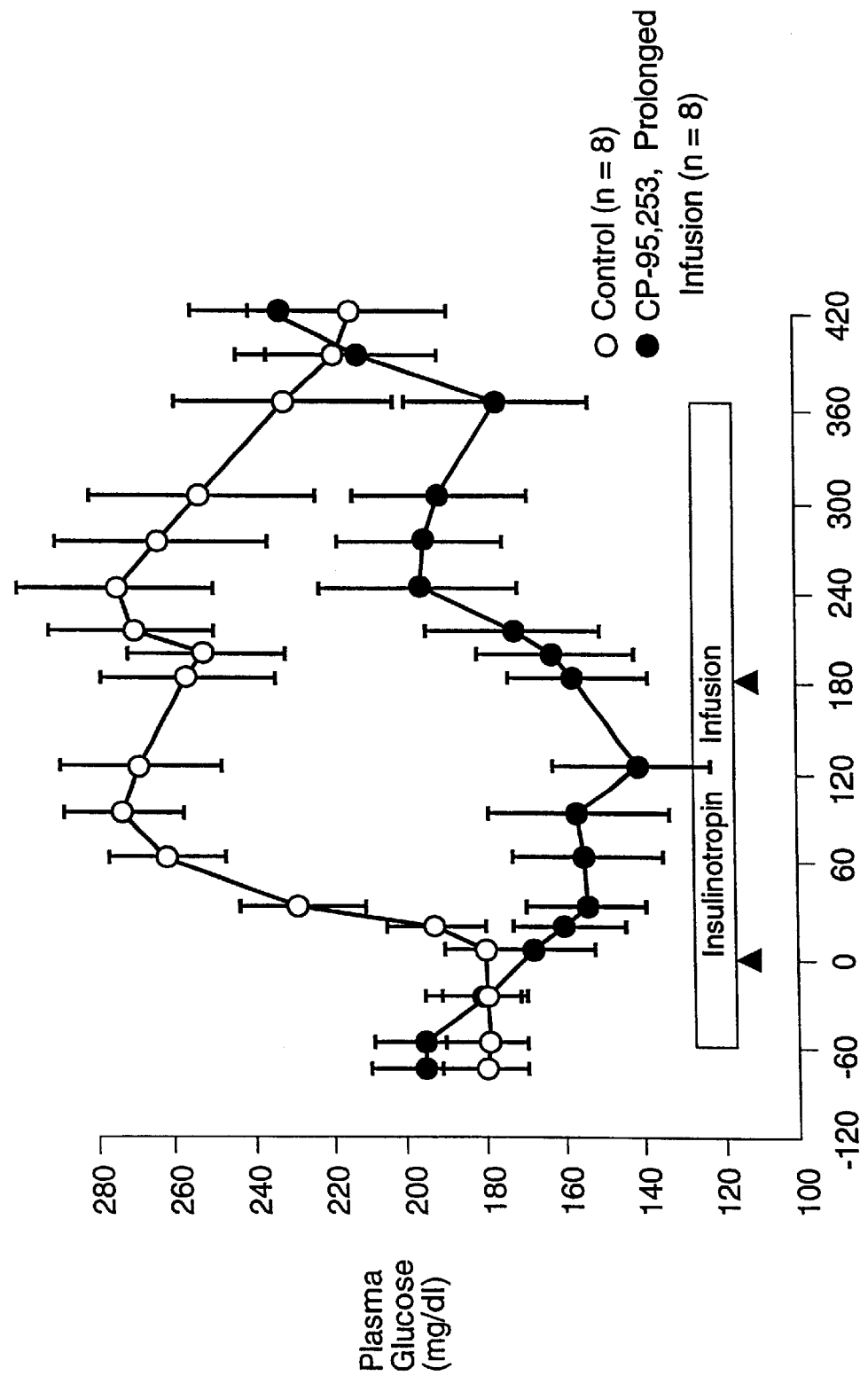
FIG. 1 shows the effect of a prolonged infusion (7 hours) of 4 ng/kg/min insulinotropin on plasma glucose levels in patients with NIDDM.
Figure 2:
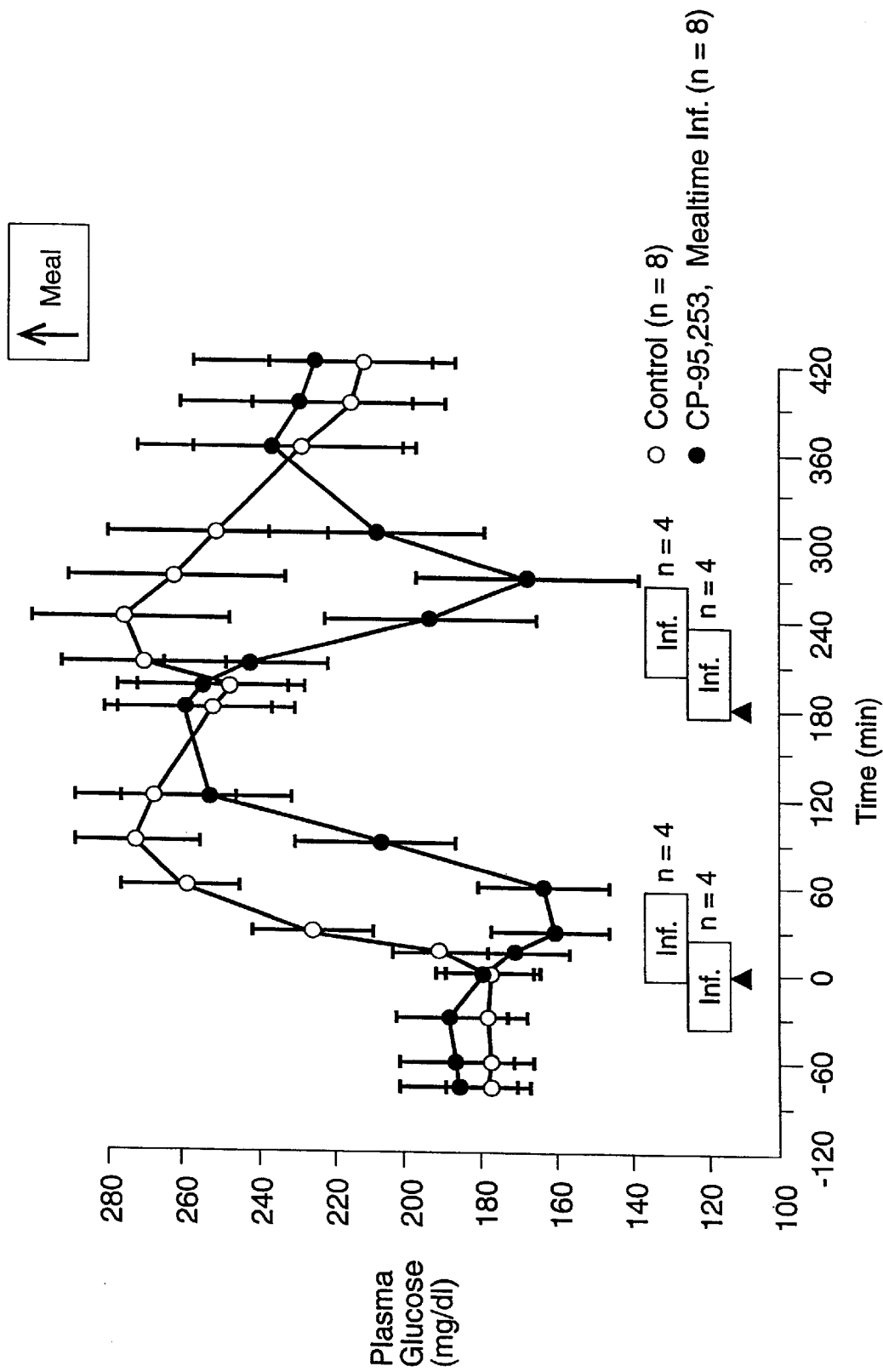
FIG. 2 shows the effect of a short infusion (60 minutes) of 10 ng/kg/min insulinotropin on plasma glucose levels in patients with NIDDM.
Figure 3:
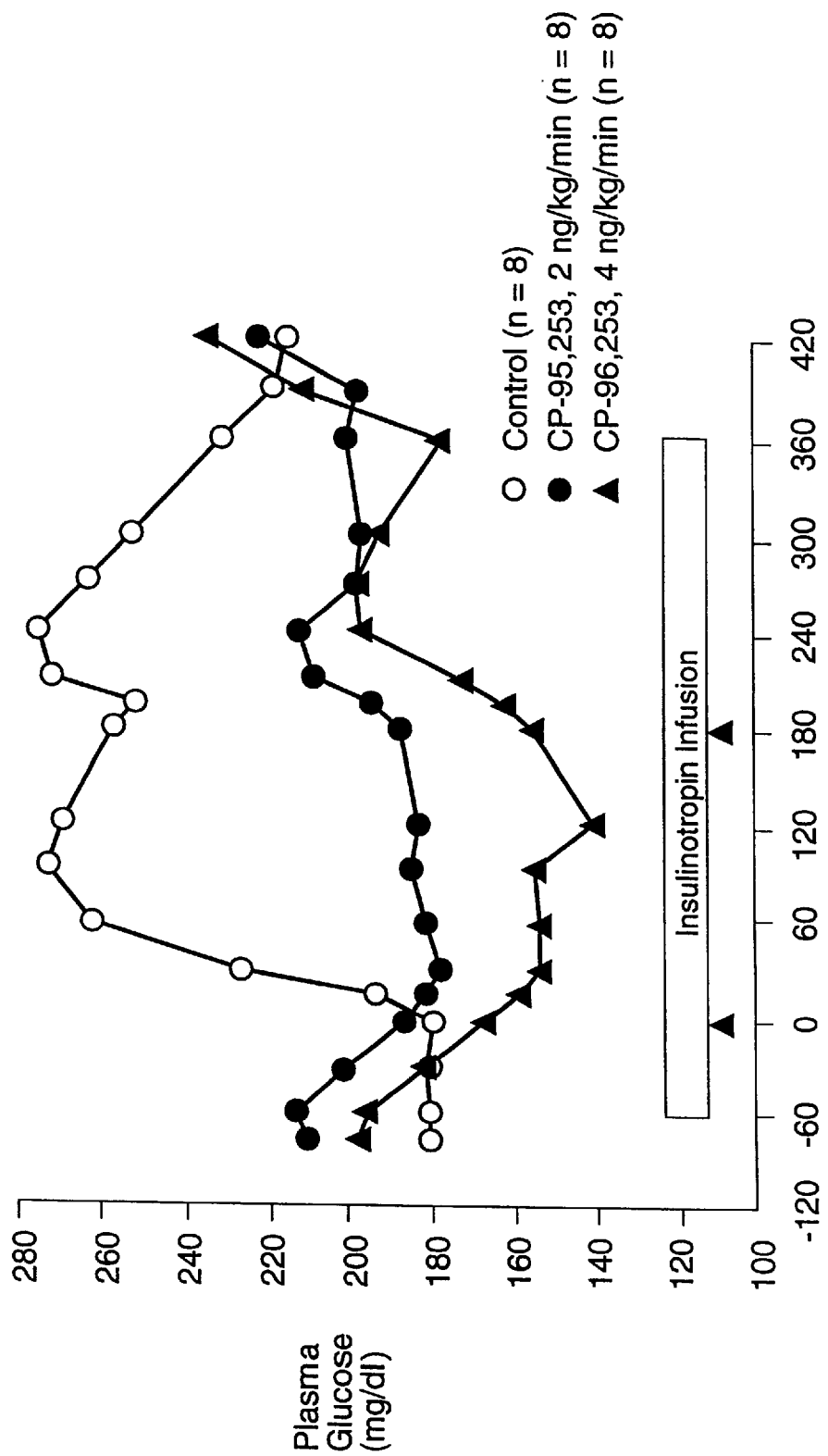
FIG. 3 shows the effect of a prolonged infusion (7 hours) of 2 ng/kg/min and 4 ng/kg/min of insulinotropin on plasma glucose levels in patients with NIDDM.
Figure 4:
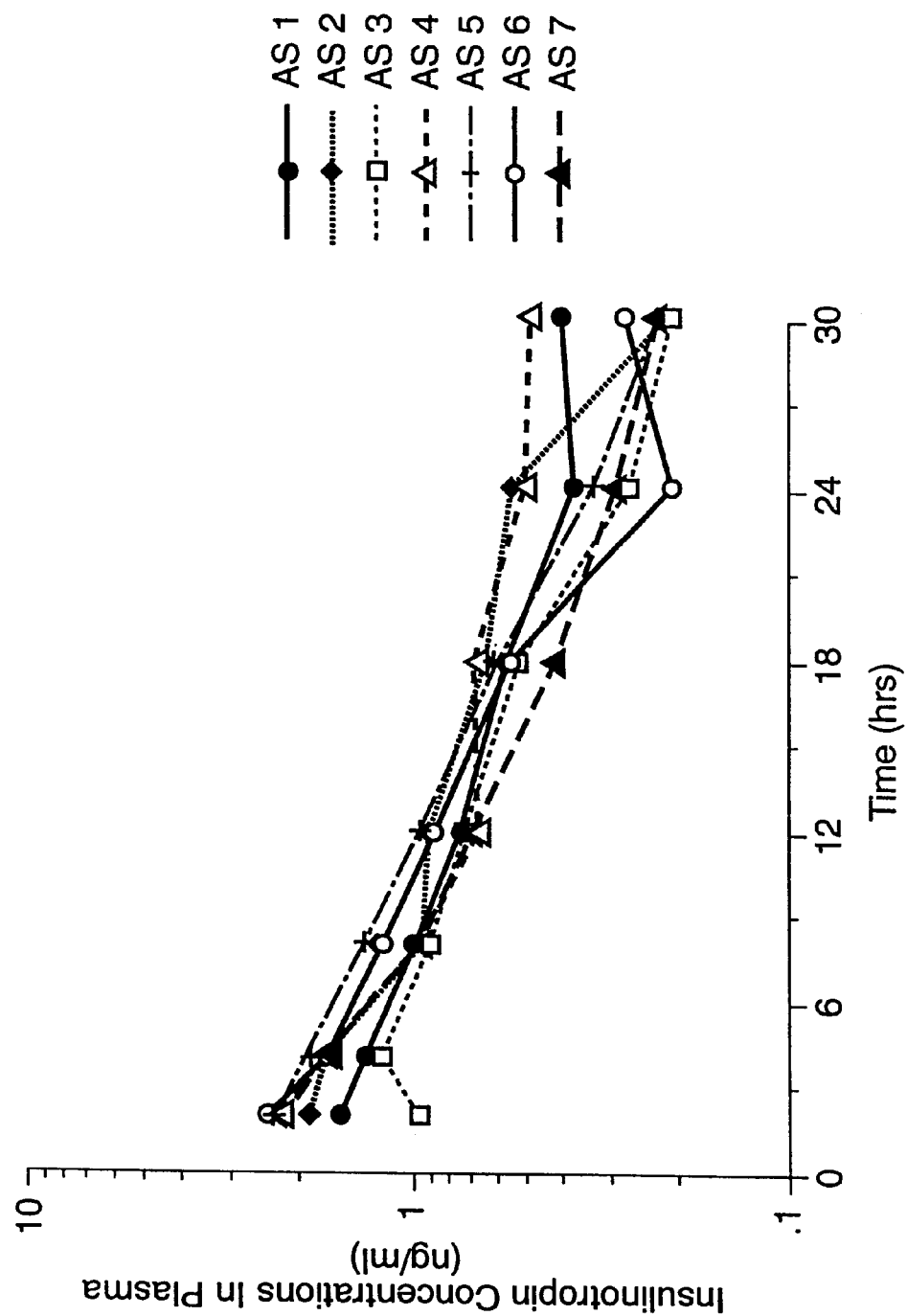
FIG. 4. Mean (n=3) Plasma Concentration of Insulinotropin in Rats After Subcutaneous Administration of Single 0.5 mg/0.5 ml Doses in Different Aqueous Suspensions (AS).
Figure 5:
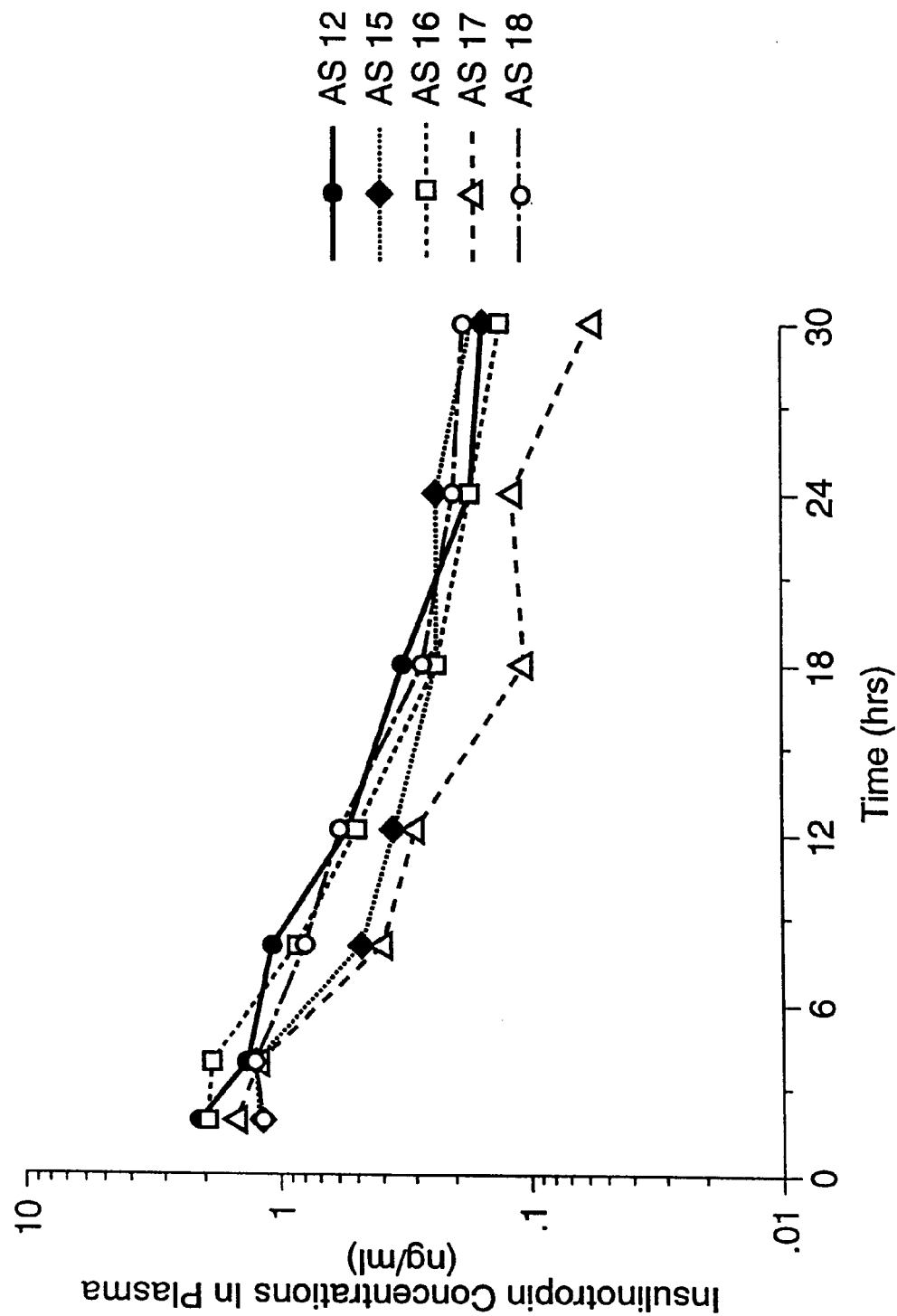
FIG. 5. Mean (n=3) Plasma Concentration of Insulinotropin in Rats After Subcutaneous Administration of Single 0.5 mg/0.5 ml Doses in Different Aqueous Suspensions (AS).
Figure 6:
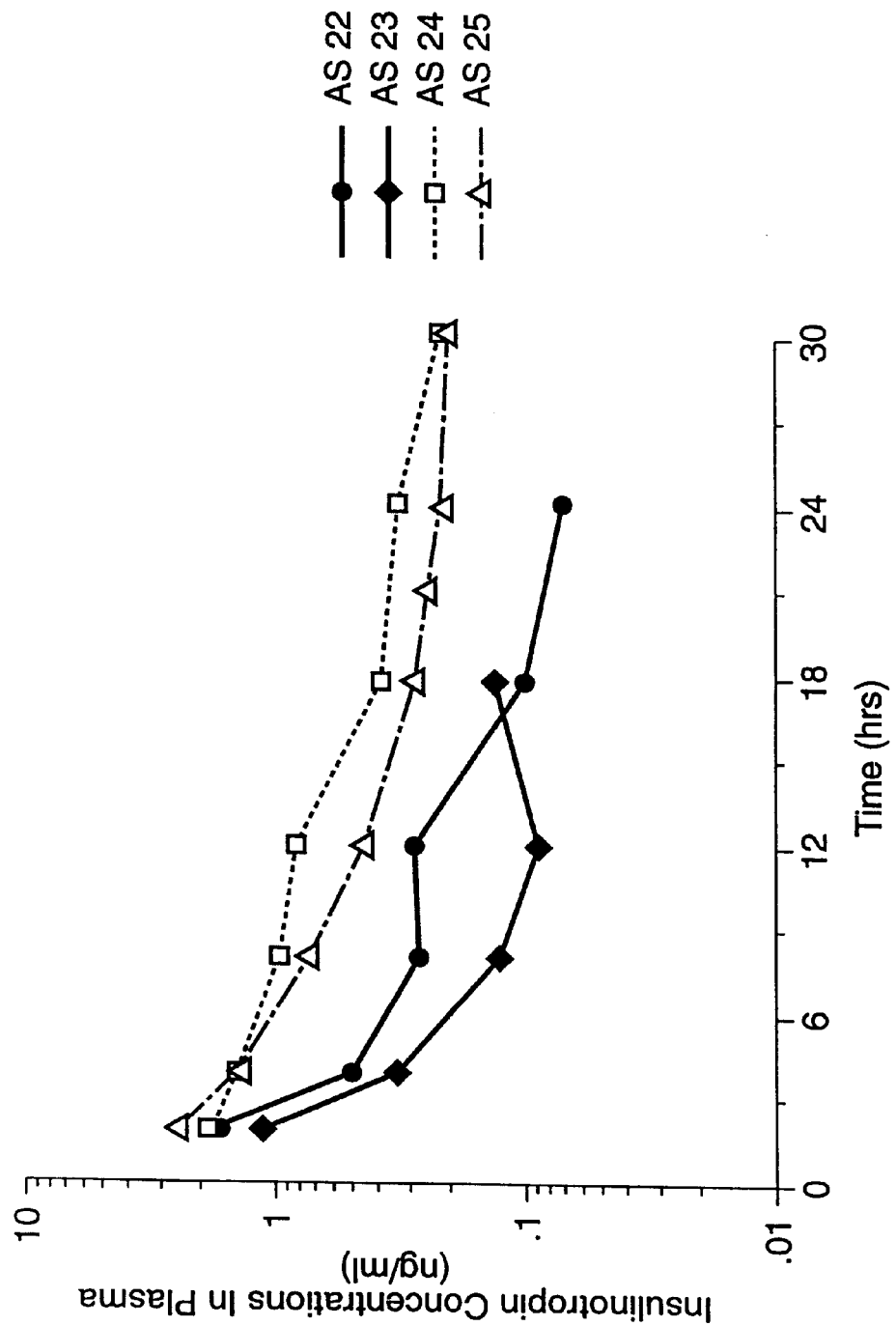
FIG. 6. Mean (n=3) Plasma Concentration of Insulinotropin in Rats After Subcutaneous Administration of Single 0.5 mg/0.5 ml Doses in Different Aqueous Suspensions (AS).
Figure 7:
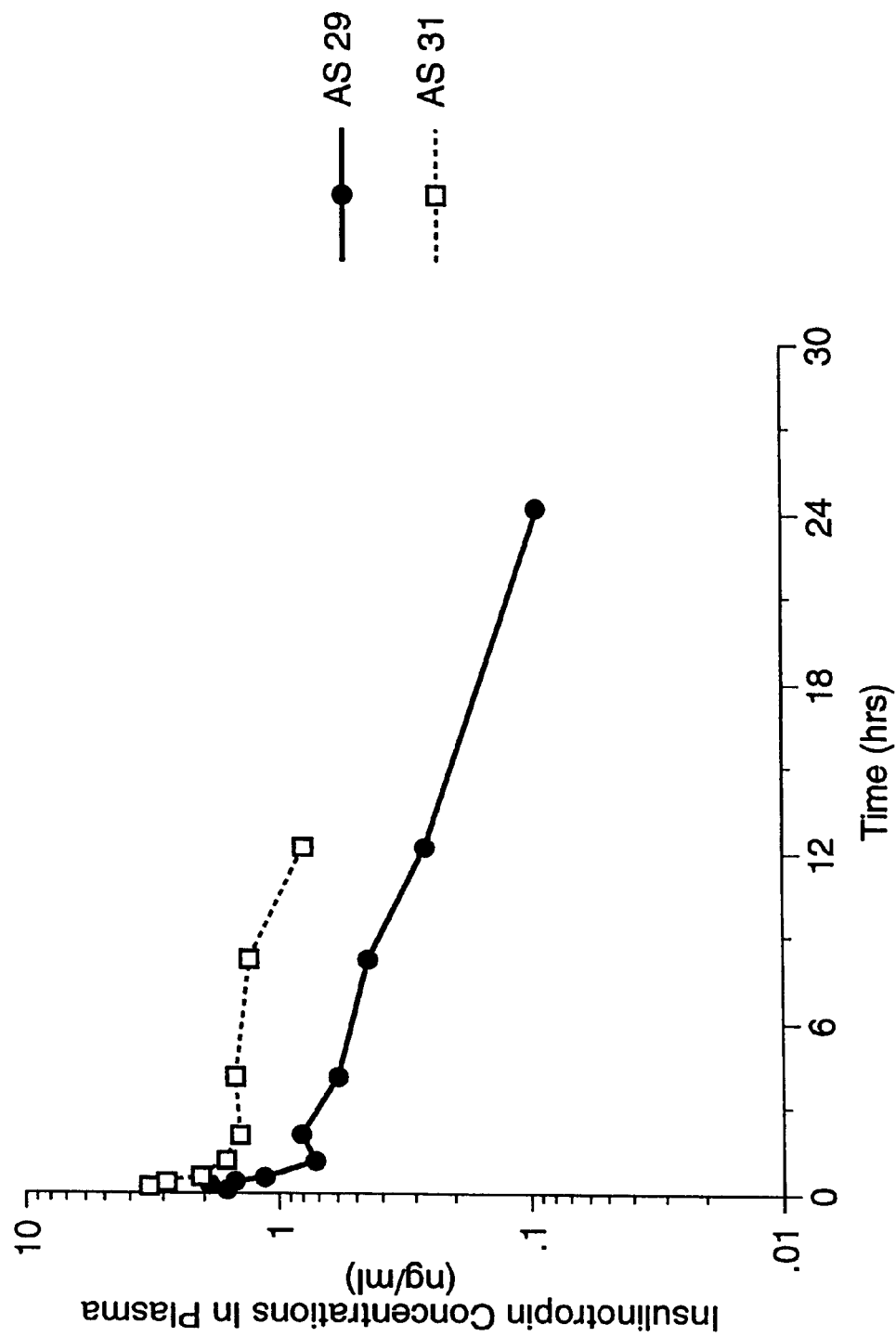
FIG. 7. Mean (n=3) Plasma Concentration of Insulinotropin in Rats After Subcutaneous Administration of Single 0.5 mg/0.5 ml Doses in Different Aqueous Suspensions (AS).

In one embodiment, the present invention is directed to a method for the treatment of non-insulin dependent diabetes mellitus in a mammal in need of such treatment comprising the repeated administration over an extended period of time of a compound with prolonged action after each administration, said prolonged action necessary to achieve sustained glycemic control in such mammals, said compound selected from the group consisting of:

(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)

(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)

wherein X is selected from the group consisting of:
(A) Lys,
(B) Lys-Gly, and
(C) Lys-Gly-Arg;
(c) a derivative of a polypeptide comprising the primary structure

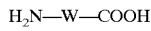

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which derivative when processed in a mammal results in a polypeptide derivative having an insulinotropic activity;
(d) a derivative of a polypeptide comprising the primary structure

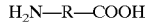

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQUENCE ID NO: 3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQUENCE ID NO: 4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQUENCE ID NO: 5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide.

Preferred is the method wherein said administration is subcutaneous.

Also preferred is the method wherein said administration is intramuscular.

Also preferred is the method wherein said administration is transdermal.

Also especially preferred is the method wherein said administration is by an infusion pump.

Also preferred is the method wherein said administration is by oral inhalation.

Also preferred is the method wherein said administration is by nasal inhalation.

Also preferred is the method wherein said administration is gastrointestinal.

In another embodiment, the present invention is directed to a composition of matter comprising;
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly, and
(C) Lys-Gly-Arg;
(c) a derivative of a polypeptide comprising the primary structure

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which derivative when processed in a mammal results in a polypeptide derivative having an insulinotropic activity;
(d) a derivative of a polypeptide comprising the primary structure

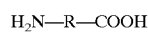

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5);
a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide, and
(ii) a polymer capable of prolonging the action of said compound to achieve sustained glycemic control.

Especially preferred is the composition wherein said polymer is a low molecular weight polymer.

Further especially preferred is a composition wherein said polymer is selected from the group consisting of polyethylene glycol, polyvinylpyrrolidone, polyvinylalcohol, polyoxyethylene-polyoxypropylene copolymers, polysaccharides selected from the group consisting of cellulose, cellulose derivatives, chitosan, acacia gum, karaya gum, guar gum, xanthan gum, tragacanth, alginic acid, carrageenan, agarose, and furcellarans, dextran, starch, starch derivatives, hyaluronic acid, polyesters, polyamides, polyanhydrides, and polyortho esters, with especially preferred polymers selected from the group consisting of polyethylene glycol and polyvinylpyrrolidone.

In another embodiment, the present invention is directed to a composition of matter comprising;
  (i) a compound selected from the group consisting of:
    (a) a peptide having the amino acid sequence:
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
    (b) a peptide having the amino acid sequence:
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
    wherein X is selected from the group consisting of:
      (A) Lys,
      (B) Lys-Gly, and
      (C) Lys-Gly-Arg;
    (c) a derivative of a polypeptide comprising the primary structure

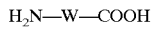

wherein W is an amino acid sequence selected from the group consisting of
    His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
    His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
    which derivative when processed in a mammal results in a polypeptide derivative having an insulinotropic activity;
    (d) a derivative of a polypeptide comprising the primary structure

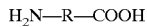

wherein R is an amino acid sequence selected from the group consisting of
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO:2);
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3);
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4); and
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and
    a derivative of said peptides (a) through (d) wherein said derivative is selected from the group consisting of:
      (1) a pharmaceutically acceptable acid addition salt of said peptides;
      (2) a pharmaceutically acceptable carboxylate salt of said peptides;
      (3) a pharmaceutically acceptable alkali addition salt of said peptides;
      (4) a pharmaceutically acceptable lower alkyl ester of said peptides; and
      (5) a pharmaceutically acceptable amide of said peptides wherein said pharmaceutically acceptable amide is selected from the group consisting of amide, lower alkyl amide and lower dialkyl amide, and
  (ii) a pharmaceutically acceptable water-immiscible oil suspension capable of prolonging administration of said compound.

Especially preferred is the composition wherein said oil is selected from the group consisting of peanut oil, sesame oil, almond oil, castor oil, camellia oil, cotton seed oil, olive oil, corn oil, soy oil, safflower oil, coconut oil, esters of fatty acids, and esters of fatty alcohols.

Further especially preferred is the composition further comprising a wetting agent, especially a nonionic surfactant.

More further especially preferred is the composition further comprising a suspending agent.

In another embodiment, the present invention is directed to a composition of matter comprising;
  (i) a compound selected from the group consisting of:
    (a) a peptide having the amino acid sequence:
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
    (b) a peptide having the amino acid sequence:
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
    wherein X is selected from the group consisting of:
      (A) Lys,
      (B) Lys-Gly, and
      (C) Lys-Gly-Arg;
    (c) a derivative of a polypeptide comprising the primary structure

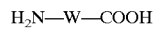

wherein W is an amino acid sequence selected from the group consisting of
    His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
    His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
    which derivative when processed in a mammal results in a polypeptide derivative having an insulinotropic activity;
    (d) a derivative of a polypeptide comprising the primary structure

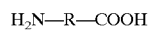

wherein R is an amino acid sequence selected from the group consisting of
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2)

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3)

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4) and His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and a derivative of said peptides (a) through (d) wherein said derivative is selected from the group consisting of:

(1) a pharmaceutically acceptable acid addition salt of said peptides;

(2) a pharmaceutically acceptable carboxylate salt of said peptides;

(3) a pharmaceutically acceptable alkali addition salt of said peptides;

(4) a pharmaceutically acceptable lower alkyl ester of said peptides; and (5) a pharmaceutically acceptable amide of said peptides wherein said pharmaceutically acceptable amide is selected from the group consisting of amide, lower alkyl amide and lower dialkyl amide, and (ii) zinc (II), which is complexed with the peptide.

Preferred is the composition capable of sustained glycemic action.

Especially preferred is the composition wherein the zinc product is amorphous.

Also especially preferred is the composition wherein the zinc product is crystalline.

In yet another embodiment, the present invention is directed to a composition of matter comprising;

(i) a compound selected from the group consisting of:

(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);

(b) a peptide having the amino acid sequence:
His-Ala-Glu-Gly-Thr-Phe-Thr-Ser-Asp-Val-Ser-Ser-Tyr-Leu-Glu-Gly-Gin-Ala-Ala-Lys-Glu-Phe-Ile-Ala-Trp-Leu-Val-X (SEQUENCE ID NO: 7)

wherein X is selected from the group consisting of:
(A) Lys,
(B) Lys-Gly, and
(C) Lys-Gly-Arg;

(c) a derivative of a polypeptide comprising the primary structure

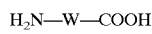

H₂N—W—COOH wherein W is an amino acid sequence selected from the group consisting of His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)

and which derivative when processed in a mammal results in a polypeptide derivative having an insulinotropic activity;

(d) a derivative of a polypeptide comprising the primary structure

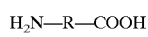

H₂N—R—COOH wherein R is an amino acid sequence selected from the group consisting of His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2)

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3)

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4) and His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and a derivative of said peptides (a) through (d) wherein said derivative is selected from the group consisting of:

(1) a pharmaceutically acceptable acid addition salt of said peptides;

(2) a pharmaceutically acceptable carboxylate salt of said peptides;

(3) a pharmaceutically acceptable alkali addition salt of said peptides;

(4) a pharmaceutically acceptable lower alkyl ester of said peptides; and (5) a pharmaceutically acceptable amide of said peptides wherein said pharmaceutically acceptable amide is selected from the group consisting of amide, lower alkyl amide and lower dialkyl amide, and (ii) a metal selected from the group consisting of Ni (II), Co (II), Mg (II), Ca (II), K (I), Mn (II), Fe(II), and Cu(II).

In yet another embodiment, the present invention is directed to a composition of matter comprising;

(i) a compound selected from the group consisting of:

(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);

(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)

wherein X is selected from the group consisting of:
(A) Lys,
(B) Lys-Gly-,
(C) Lys-Gly-Arg;

(c) a derivative of a polypeptide comprising the primary structure

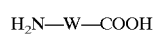

H₂N—W—COOH wherein W is an amino acid sequence selected from the group consisting of His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)

which derivative when processed in a mammal results in a polypeptide derivative having an insulinotropic activity;

(d) a derivative of a polypeptide comprising the primary structure

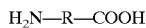

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4); and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and
a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide, and
(ii) a basic polypeptide, wherein such composition is an aqueous suspension capable of sustained glycemic control.

Especially preferred is the composition wherein the basic polypeptide is protamine.

In yet another embodiment, the present invention is directed to a composition of matter comprising;
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly,
(C) Lys-Gly-Arg;
(c) a derivative of a polypeptide comprising the primary structure

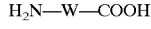

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 7)
which derivative when processed in a mammal results in a polypeptide derivative having an insulinotropic activity;
(d) a derivative of a polypeptide comprising the primary structure

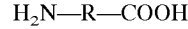

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4); and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and
a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide, and
(ii) a phenolic compound, wherein such composition is an aqueous suspension capable of sustained glycemic control.

Especially preferred is the composition wherein said phenolic compound is selected from the group consisting of phenol, cresol, resorcinol, and methyl/araben.

In yet another embodiment, the present invention is directed to a composition of matter comprising;
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly,
(C) Lys-Gly-Arg;
(c) a derivative of a polypeptide comprising the primary structure

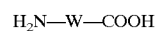

wherein W is an amino acid sequence selected from the group consisting of

His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)

which derivative when processed in a mammal results in a polypeptide derivative having an insulinotropic activity;

(d) a derivative of a polypeptide comprising the primary structure

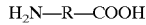

wherein R is an amino acid sequence selected from the group consisting of

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3);

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4); and His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and a derivative of said peptides (a) through (d) wherein said derivative is selected from the group consisting of:

(1) a pharmaceutically acceptable acid addition salt of said peptides;

(2) a pharmaceutically acceptable carboxylate salt of said peptides;

(3) a pharmaceutically acceptable alkali addition salt of said peptides;

(4) a pharmaceutically acceptable lower alkyl ester of said peptides; and (5) a pharmaceutically acceptable amide of said peptides wherein said pharmaceutically acceptable amide is selected from the group consisting of amide, lower alkyl amide and lower dialkyl amide, and (ii) a basic polypeptide and a phenolic compound, wherein such composition is an aqueous suspension capable of sustained glycemic control.

In another embodiment, the present invention is directed to a composition of matter comprising;

(i) a compound selected from the group consisting of:

(a) a peptide having the amino acid sequence:

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)

(b) a peptide having the amino acid sequence:

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)

wherein X is selected from the group consisting of:

(A) Lys, (B) Lys-Gly, and (C) Lys-Gly-Arg;

(c) a derivative of a polypeptide comprising the primary structure

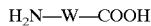

wherein W is an amino acid sequence selected from the group consisting of

His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)

which derivative when processed in a mammal results in a polypeptide derivative having an insulinotropic activity;

(d) a derivative of a polypeptide comprising the primary structure

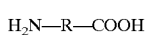

wherein R is an amino acid sequence selected from the group consisting of

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQUENCE ID NO: 3)

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQUENCE ID NO: 4) and His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQUENCE ID NO: 5) and a derivative of said peptides (a) through (d) wherein said derivative is selected from the group consisting of:

(1) a pharmaceutically acceptable acid addition salt of said peptides;

(2) a pharmaceutically acceptable carboxylate salt of said peptides;

(3) a pharmaceutically acceptable alkali addition salt of said peptides;

(4) a pharmaceutically acceptable lower alkyl ester of said peptides; and (5) a pharmaceutically acceptable amide of said peptides wherein said pharmaceutically acceptable amide is selected from the group consisting of amide, lower alkyl amide and lower dialkyl amide, and (ii) a basic polypeptide, a phenolic compound, and a metal ion wherein said composition is an aqueous suspension capable of sustained glycemic control.

Preferred is the composition wherein said basic polypeptide is protamine.

Also preferred is the composition wherein said metal ion is zinc.

In another embodiment, the present invention is directed to a composition of matter comprising;

(i) a compound selected from the group consisting of:

(a) a peptide having the amino acid sequence:

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);

(b) a peptide having the amino acid sequence:

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)

wherein X is selected from the group consisting of:

(A) Lys, (B) Lys-Gly, (C) Lys-Gly-Arg;

(c) a derivative of a polypeptide comprising the primary structure

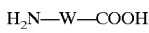

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which derivative when processed in a mammal results in a polypeptide derivative having an insulinotropic activity;

(d) a derivative of a polypeptide comprising the primary structure

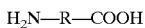

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4); and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and
a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide, and
(ii) said peptides and derivatives thereof having been subjected to conditions resulting in amorphous crystalline formation.

Preferred is the composition wherein said conditions are high shear, exposure to salts; or combinations thereof.

Especially preferred is the composition wherein said salt is selected from the group consisting of ammonium sulfate, sodium sulfate, lithium sulfate, lithium chloride, sodium citrate, ammonium citrate, sodium phosphate, potassium phosphate, sodium chloride, potassium chloride, ammonium chloride, sodium acetate, ammonium acetate, magnesium sulfate, calcium chloride, ammonium nitrate, and sodium formate; and combinations thereof.

In still another embodiment, the present invention is directed to a composition of matter comprising;

(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly,
(C) Lys-Gly-Arg;
(c) a derivative of a polypeptide comprising the primary structure

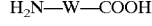

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which derivative when processed in a mammal results in a polypeptide derivative having an insulinotropic activity;

(d) a derivative of a polypeptide comprising the primary structure

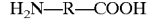

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 2);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 3);
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQUENCE ID NO: 4); and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQUENCE ID NO: 5); and
a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide, and
(ii) a liposome delivery system.
Especially preferred is the composition wherein said liposome is phospholipid based.

Also especially preferred is the composition wherein said liposome is non-phospholipid based.

The present invention is also directed to the treatment of non-insulin dependent diabetes mellitus in a mammal in need of such treatment comprising the prolonged administration of the compositions of the present invention.

DETAILED DESCRIPTION OF THE INVENTION

Unless otherwise indicated, the term "derivative", as used throughout this Specification and the appendant claims, includes, but is not limited to, polypeptides comprising the primary structure shown, wherein one or more L-amino acids are included at the C-terminus thereof; wherein the C-terminal carboxyl group forms an ester with a $(C_1-C_6)$ straight or branched chain alkyl group; wherein the C-terminal carboxyl group forms a carboxamide or substituted carboxamide; wherein the acidic amino acid residues (Asp and/or Glu) form an ester or carboxamide; and combinations thereof.

Included within the scope of this invention are polypeptides having homology to the peptides described above, which homology is sufficient to impart insulinotropic activity to such polypeptides. Also included within the scope of this invention are variants of the polypeptides described above, which variants comprise inconsequential amino acid substitutions and have insulinotropic activity.

Glucagon-like Peptide-1 (7–37), its isolation, characterization, and use to treat Diabetes mellitus are disclosed in U.S. Pat. Nos. 5,118,666 and 5,120,712, the disclosures of these patents in their entirety being incorporated herein by reference.

In the present invention, it has now been discovered that prolonged plasma elevations of GLP-1, and related polypeptides, are necessary during the meal and beyond to achieve sustained glycemic control in patients with Non Insulin Dependent Diabetes Mellitus. It has surprisingly been found that raising GLP-1, and related peptides, around meal time alone, even for periods of up to one hour, will not adequately control the glucose levels. Thus, administration of GLP-1, and related peptides, requires a prolonged delivery system. This prolonged delivery system leads to an enhancing of insulin action.

The phrase "enhancing insulin action", as used throughout this Specification and the appendant claims, includes, but is not limited to, one or more of increasing insulin synthesis, increasing insulin secretion, increasing glucose uptake by muscle and fat and decreasing glucose production by the liver.

The polypeptides of this invention are prepared by various methods well known to those skilled in the art. For example, the polypeptides can be synthesized using automated peptide synthesizers such as an Applied Biosystems (ABI) 430A solid phase peptide synthesizer. Alternatively, the polypeptides of this invention can be prepared using recombinant DNA technology wherein a DNA sequence coding for the polypeptide is operably linked to an expression vector and used to transform an appropriate host cell. The transformed host cell is then cultured under conditions whereby the polypeptide will be expressed. The polypeptide is then recovered from the culture. Further still, a combination of synthesis and recombinant DNA techniques can be employed to produce the amide and ester derivatives of this invention and/or to produce fragments of the desired polypeptide which are then joined by methods well known to those skilled in the art.

Derivatives of the polypeptides according to this invention are prepared by methods well known to those skilled in the art. For example, C-terminal alkyl ester derivatives of the polypeptides of this invention are prepared by reacting the desired $(C_1-C_6)$alkanol with the desired polypeptide in the presence of a catalytic acid such as HCl. Appropriate reaction conditions for such alkyl ester formation include a reaction temperature of about 50° C. and reaction times of about 1 hour to about 3 hours. Similarly, derivatives of the polypeptides of this invention comprising $(C_1-C_6)$alkyl esters of the Asp and/or Glu residues within the polypeptide can be so formed.

Carboxamide derivatives of the polypeptides of this invention are also prepared by solid phase peptide synthesis methods well known to those skilled in the art. For example, see, *Solid Phase Peptide Synthesis,* Stewart, J. M. et al., Pierce Chem. Co. Press, 1984.

Alternatively, or in combination with the above, derivatives of the polypeptides of this invention can be prepared by modifying the DNA coding sequence for such polypeptide so that a basic amino acid residue is replaced with a different basic amino acid residue or with an acid acidic or neutral amino acid residue, or an acidic amino acid residue is replaced with a different acidic amino acid residue or with a basic or neutral amino acid residue, or a neutral amino acid residue is replaced with a different neutral amino acid residue or with an acidic or basic amino acid residue. Such changes in polypeptide primary sequence can also be accomplished by direct synthesis of the derivative. Such methods are well known to those skilled in the art. Of course, such derivatives, to be useful in the practice of this invention, must achieve an insulinotropic effect.

The insulinotropic activity of a polypeptide derivative according to this invention is determined as follows.

Pancreatic islets are isolated from pancreatic tissue from normal rats by a modification of the method of Lacy, P. E., et al., *Diabetes,* 16:35–39 (1967) in which the collagenase digest of pancreatic tissue is separated on a Ficoll gradient (27%, 23%, 20.5% and 11% in Hanks' balanced salt solution, pH 7.4). The islets are collected from the 20.5%/ 11% interface, washed and handpicked free of exocrine and other tissue under a stereomicroscope. The islets are incubated overnight in RPMI 1640 medium supplemented with 10% fetal bovine serum and containing 11 mM glucose at 37° C. and 95% air/5% $CO_2$. The islets are then transferred to RPMI 1640 medium supplemented with 10% fetal bovine serum and containing 5.6 mM glucose. The islets are incubated for 60 minutes at 37° C., 95% air/5% $CO_2$. The polypeptide derivative to be studied is prepared at 1 nM and 10 nM concentrations in RPMI medium containing 10% fetal bovine serum and 16.7 mM glucose. About 8 to 10 isolated islets are then transferred by pipette to a total volume of 250 µl of the polypeptide derivative containing medium in 96 well microtiter dishes. The islets are incubated in the presence of the polypeptide derivative at 37° C., 95% air/5% $CO_2$ for 90 minutes. Then, aliquots of islet-free medium are collected and 100 µl thereof are assayed for the amount of insulin present by radioimmunoassay using an Equate Insulin RIA Kit (Binax, Inc., Portland, Me.).

Dosages effective in treatment of adult onset diabetes will range from about 1 pg/kg to 1,000 µg/kg per day when a polypeptide derivative of this invention is administered, for example, intravenously, intramuscularly or subcutaneously. A preferred dosage range for intravenous infusion during and between meals is about 4 to 10 ng/kg/min or about 0.6 to 1.4 µg/day based on a 100 kg patient. It is to be appreciated, however, that dosages outside of that range are possible and are also within the scope of this invention. The appropriate dosage can and will be determined by the prescribing physician and will be a result of the severity of the condition being treated as well as the response achieved with the derivative being administered and the age, weight, sex and medical history of the patient.

The prolonged administration may be achieved by subcutaneous, intramuscular, or transdermal means, oral inhalation, nasal inhalation, gastrointestinal, or by means of an infusion pump.

Prolonged administration of GLP-1, and related peptides, may also be achieved by formulation as a solution in various water-soluble polymers. These polymers are generally low molecular weight (<15 kDa) polymers. Non-limiting examples of such low molecular weight polymers include polyethylene glycol, polyvinylpyrrolidone, polyvinylalcohol and polyoxyethylene-polyoxypropylene copolymers. Higher molecular weight polymers may be used. Non-limiting examples of higher molecular weight polymers include polysaccharides such as cellulose and its derivatives, chitosan, acacia gum, karaya gum, guar gum, xanthan gum, tragacanth, alginic acid, carrageenan, agarose, furcelleran. In the later case, polymers which are degraded in vivo either enzymatically or by hydrolysis are preferred, for example, dextran; starch and its derivatives, hyaluronic acid, polyesters, polyamides, polyanhydrides and polyortho esters. The tissue accumulation associated with high molecular weight, non-biodegradable polymers is avoided by using low molecular weight polymers or biodegradable polymers. The formulations typically contain GLP-1, or related peptides, at approximately 1 mg/ml, with concentration dependent on the polymer, but typically at concentrations up to that which will attain a 50 cps viscosity, and possibly a suitable buffer, tonicity agent, and preservative. In vivo data in rats and man demonstrate that the formulations are capable of achieving measurable blood insulinotropin, for example, levels for up to 24 hours. In contrast, insulinotropin, for example, formulated in phosphate-buffered saline results in rapid (~15 minutes) peak plasma levels, with plasma level dropping below detection limits in just over 4 hours. Plasma concentration versus time plots suggest that insulinotropin absorption rate, for example, from the injection site has been significantly reduced in the presence of the polymers.

GLP-1, and related peptides, may also be formulated as particles suspended in a pharmaceutically acceptable oil. The preferred oils are triglycerides. Non-limiting examples of such oils include peanut oil, sesame oil, almond oil, castor oil, camellia oil, cotton seed oil, olive oil, corn oil, soy oil, safflower oil, and coconut oil. Oils of other classes are acceptable, for example, esters of fatty acids and esters of fatty alcohols, as long as the oil is immiscible with water and is a poor solvent for the peptide. The formulation may also contain appropriate preservatives, wetting agents, and suspending agents. The weight percent of insulinotropin, for example, in the formulation may vary from 0.01 to 10%. In vivo data in rats demonstrate that these formulations are capable of achieving measurable insulinotropin blood levels, for example, for up to 24 hours. In contrast, insulinotropin, for example, formulated in phosphate-buffered saline results in rapid (~15 minutes) peak plasma levels, with plasma level dropping below detection limits in just over 4 hours. Plasma concentration versus time plots suggest that insulinotropin absorption rate from the injection site have been significantly reduced in the oil suspensions.

GLP-1, and related peptides, may also be formulated as a low solubility form for administration by combination with a metal ion, preferably in the form of a salt. A preferred ion is zinc (II). The combination may result in a composition which is amorphous or crystalline. Other metal ions may also be used including Ni(II), Co(II), Mg(II), Ca(II), K(I), Mn(II), Fe(II) and Cu(II).

Other forms of prolonged administration include liposomes, either multilamellar or unilamellar, the preparation of which is well known to those skilled in the art. The liposomes, whether multilamellar or unilamellar, may be phospholipid or non-phospholipid based.

Another type of prolonged delivery formulation is an aqueous suspension of insulinotropin precipitates or aggregates formed by using precipitants for example, phenolic compounds or basic polypeptides or metal ions or salts, and/or by using high shear. More than one precipitant can be used at one time. The precipitates can be either crystalline or amorphous.

Insulinotropin crystals can be obtained from a solution of the drug in water by using pH gradient (either high to low or low to high) and/or temperature gradient and/or salts to reduce solubility. The salts include ammonium citrate, sodium or potassium phosphate, sodium or potassium or ammonium chloride, sodium or ammonium acetate, magnesium sulfate, calcium chloride, ammonium nitrate, sodium formate, and any other salts which can reduce the solubility of the drug. If the salt used for crystallization is not pharmaceutically acceptable, the mother liquor can be substituted by pharmaceutically acceptable medium after crystallization is completed. If further reduction of drug solubility is necessary to achieve a desirable pharmacokinetic profile, the crystals can be treated by metal ions such as zinc or calcium and/or phenolic compounds. The treatment can be done by simply incorporating those additives to the crystal suspension.

The solubility of the insulinotropin precipitates or aggregates can range from less than 1 µg/mL to 500 µg/mL under physiological conditions. In vivo data in rats demonstrate that the formulations are capable of achieving measurable insulinotropin blood levels, for example, for at least 30 hours.

Aqueous media used for the above formulations can be any kind of buffer system which can be used for injection or even with pure water. The pH of the final formulation can be any value as long as the formulation is injectable. Protamine can be added as any kind of salt form (e.g. sulfate, chloride, etc.) or protamine base. Exemplary concentration ranges of the components which can be used for the formulation preparation are as follows: phenol (0.5 to 5.0 mg/ml), m-cresol (0.5 to 5.5 mg/ml), protamine (0.02 to 1.0 mg/ml), zinc (0.10 to 6 zinc/insulinotropin molar ratio), sodium chloride (up to 100 mg/ml), and phosphate buffer (5–500 mM).

Other phenolic on non phenolic compounds may also be used. Non-limiting examples of such compounds include resorcinol, methylparaben, propylparaben, benzyl alcohol, chlorocresol, cresol, benzaldehyde, catecol, pyrogallol, hydroquinone, n-propyl gallate, butylated hydroxyanisole, butylated hydroxytoluene. Non-limiting examples of basic polypeptides are polylysine, polyarginine, etc.

Having described the invention in general terms, reference is now made to specific examples. It is to be understood that these examples are not meant to limit the present invention, the scope of which is determined by the appended claims.

EXAMPLE 1

Insulinotropin (1 mg/ml) Suspension

Solution A1 Preparation 10 mg of insulinotropin was weighed into a 5 ml volumetric flask. Approximately 4 ml of phosphate buffered saline (PBS) was added to the flask to disperse and dissolve the drug. Sufficient PBS (q.s. amount) was added to fill the flask. 20 mg of insulinotropin was weighed into a 10 ml volumetric flask. Approximately 8 ml of PBS was added to the flask to disperse and dissolve the drug. The q.s. amount of PBS was added to the flask. The volumes in both flasks were combined by filtering them by a glass syringe through a 0.22μ filter (low protein binding) into a 10 ml glass vial. Solution A1 contained insulinotropin 2 mg/ml in PBS.

Solution B1 Preparation 8 mg of protamine sulfate and 44 mg of phenol were weighed into a 10 ml volumetric flask. The q.s. amount of PBS was added to dissolve the protamine sulfate and the phenol. This solution was filtered through a 0.22μ filter (low protein binding) into a 10 ml glass vial. Solution B1 contained protamine base 0.6 mg/ml and phenol 4.4 mg/ml in PBS.

Aqueous Suspension 1

1.5 ml of solution A1 was pipetted into a 3.5 ml type I glass vial. The contents of the vial were stirred magnetically while 1.5 ml of solution B1 was pipetted into the vial. The vial was stoppered and sealed with an aluminum shell. The vial contents were stirred gently for 16 hours to allow suspension formation. Aqueous Suspension 1 contained insulinotropin 1 mg/ml, protamine base 0.3 mg/ml and phenol 2.2 mg/ml in PBS. This suspension was used for In vivo pharmacokinetic studies in rats.

EXAMPLE 2

Insulinotropin (1 mg/ml) Suspension

Solution A2 Preparation 10 mg of insulinotropin was weighed into a 5 ml volumetric flask. Approximately 4 ml of PBS was added to the flask to disperse and dissolve the drug. The q.s. amount of PBS was added to the flask. 20 mg of insulinotropin was weighed into a 10 ml volumetric flask. Approximately 8 ml of PBS was added to the flask to disperse and dissolve the drug. The q.s. amount of the PBS was added to the flask. The volumes in both flasks were combined by filtering them by a glass syringe through a 0.22μ filter into a 10 ml glass vial. Solution A2 contained insulinotropin 2 mg/ml in PBS.

Solution B2 Preparation 2 mg of protamine sulfate and 44 mg of phenol were weighed into a 10 ml volumetric flask. The q.s. amount of PBS was added to the flask to dissolve the protamine sulfate and phenol. This solution was filtered through a 0.22μ filter into a 10 ml glass vial. Solution B2 contained protamine base 0.15 mg/ml and phenol 4.4 mg/ml in PBS.

Aqueous Suspension 2

1.5 ml of solution A2 was pipetted into a 3.5 ml type I glass vial. The contents of the vial were stirred magnetically while 1.5 ml of solution B2 was pipetted into the vial. The vial was stoppered and sealed with an aluminum shell. The vial contents were stirred for 16 hours to allow suspension formation. Aqueous Suspension 2 contained insulinotropin 1 mg/ml, protamine base 0.075 mg/ml, and phenol 2.2 mg/ml in PBS. This suspension was used for in vivo pharmacokinetic studies in rats.

EXAMPLE 3

Insulinotropin (1 mg/ml) Suspension

Solution A3 Preparation 20 mg of insulinotropin was weighed into a 10 ml volumetric flask. Approximately 8 ml of PBS was added to the flask to disperse and dissolve the drug. The q.s. amount of PBS was added to the flask. Solution A3 was filtered by a syringe through a 0.22μ filter into a 10 ml glass vial. Solution A3 contained insulinotropin 2 mg/ml in PBS.

Solution B3 Preparation 8 mg of protamine sulfate, 44 mg of phenol, and 323 mg of glycerin were weighed into a 10 ml volumetric flask. The q.s. amount of PBS was added to the flask to dissolve the protamine sulfate, the phenol, and the glycerin. This solution was filtered by a syringe through a 0.22μ filter into a 10 ml glass vial. Solution B3 contained protamine base 0.6 mg/ml, phenol 4.4 mg/ml, and glycerin 32 mg/ml in PBS.

Aqueous Suspension 3

1.5 ml of Solution A3 was pipetted into a 3.5 ml type I glass vial. The contents of the vial were stirred magnetically while 1.5 ml of Solution B3 was pipetted into the vial. The vial was stoppered and sealed with an aluminum shell. The vial contents were stirred for 16 hours to allow suspension formation. Aqueous Suspension 3 contained insulinotropin 1 mg/ml, protamine base 0.3 mg/ml, phenol 2.2 mg/ml, and glycerin 16 mg/ml in PBS. This suspension was used for in vivo pharmacokinetic studies in rats.

EXAMPLE 4

Insulinotropin (1 mg/ml) Suspension

Solution A4 Preparation 20 mg of insulinotropin was weighed into a 10 ml volumetric flask. Approximately 8 ml of PBS was added to the flask to disperse and dissolve the drug. The q.s. amount of PBS was added to the flask. Solution A4 was filtered by a syringe through a 0.22μ filter (Millipore Millex-GV) into a 10 ml glass vial. Solution A4 contained insulinotropin 2 mg/ml in PBS.

Solution B4 Preparation 8 mg of protamine sulfate and 52 mg of m-cresol were weighed into a 10 ml volumetric flask. The q.s. amount of PBS was added to the flask to dissolve the protamine sulfate and the m-cresol. This solution was filtered through a 0.22μ filter into a 10 ml glass vial. Solution B4 contained protamine base 0.6 mg/ml and m-cresol 5 mg/ml in PBS.

Aqueous Suspension 4

1.5 ml of solution A4 was pipetted into a 3.5 ml type I glass vial. The contents of the vial were stirred magnetically while 1.5 ml of solution B4 was pipetted into the vial. The vial was stoppered and sealed with an aluminum shell. The vial contents were stirred for 16 hours to allow crystal formation. Aqueous Suspension 4 contained insulinotropin 1 mg/ml, protamine base 0.3 mg/ml and m-cresol 2.5 mg/ml in PBS. This suspension was used for in vivo pharmacokinetic studies in rats.

EXAMPLE 5

Insulinotropin (1 mg./ml) Suspension

Solution A5 Preparation 50 mg of insulinotropin was weighed into a 25 ml volumetric flask. Approximately 23 ml of PBS was added to the flask to disperse and dissolve the drug. The q.s. amount of PBS was added to the flask. Solution A5 was filtered by a syringe through a 0.22µ filter into a 50 ml glass vial. Solution A5 contained insulinotropin 2 mg/ml in PBS.

Phenol Stock Solution Preparation 0.44 g of phenol was weighed into a 100 ml volumetric flask. Approximately 95 ml of PBS was added to the flask to dissolve the phenol. The q.s. amount of PBS was added to the flask to dissolve the phenol. The resulting solution (4.4 mg/ml phenol) was used to prepare Solution B5.

Solution B5 Preparation

Solution B5 was prepared by filtering 25 ml of the phenol stock solution through a 0.2µ filter into a 50 ml glass vial. Solution B5 contained phenol 4.4 mg/ml in PBS.

Aqueous Suspension 5

1.25 ml of solution A5 was pipetted into a 3.5 ml type I glass vial. The contents of the vial were stirred magnetically while 1.25 ml of solution B5 was pipetted into the vial. The vial was stoppered and sealed with an aluminum shell. The vial contents were stirred for 16 hours to allow suspension formation. Aqueous Suspension 5 contained insulinotropin 1 mg/ml and phenol 2.2 mg/ml in PBS. This suspension was used for in vivo pharmacokinetic studies in rats.

EXAMPLE 6

Insulinotropin (1 mg/ml) Suspension

Solution A6 Preparation 50 mg of insulinotropin was weighed into a 25 ml volumetric flask. Approximately 23 ml of PBS was added to the flask to disperse and dissolve the drug. The q.s. amount of PBS was added to the flask. Solution A6 was filtered by a syringe through a 0.22µ filter into a 50 ml glass vial. Solution A6 contained insulinotropin 2 mg/ml in PBS.

Phenol Stock Solution Preparation 0.44 g of phenol was weighed into a 100 ml volumetric flask. Approximately 95 ml of PBS was added to the flask to dissolve the phenol. The q.s. amount of PBS was added to the flask to dissolve the phenol. The resulting solution (4.4 mg/ml phenol) was used to prepare Solution B6.

Solution B6 Preparation

Solution B6 was prepared by weighing 1.25 mg of protamine sulfate into a 25 ml volumetric flask. Approximately 20 ml of phenol stock solution was added to the flask to dissolve the protamine sulfate. The q.s. amount of phenol stock solution was added to the flask. Solution B6 was filtered through a 0.22µ filter into a 50 ml glass vial. Solution B6 contained phenol 4.4 mg/ml and protamine base 0.038 mg/ml in PBS.

Aqueous Suspension 6

1.25 ml of solution A6 was pipetted into a 3.5 ml type I glass vial. The contents of the vial were stirred magnetically while 1.25 ml of solution B6 was pipetted into the vial. The vial was stoppered and sealed with an aluminum shell. The vial contents were stirred for 16 hours to allow suspension formation. Aqueous Suspension 6 contained insulinotropin 1 mg/ml, phenol 2.2 mg/ml, and protamine base 0.019 mg/ml in PBS. This suspension was used for in vivo pharmacokinetic studies in rats.

EXAMPLE 7

Insulinotropin (1 mg/ml) Suspension

Solution A7 Preparation 50 mg of insulinotropin was weighed into a 25 ml volumetric flask. Approximately 23 ml of PBS was added to the flask to disperse and dissolve the drug. The q.s. amount of PBS was added to the flask. Solution A7 was filtered by a syringe through a 0.22µ filter into a 50 ml glass vial. Solution A7 contained insulinotropin 2 mg/ml in PBS.

Phenol Stock Solution Preparation 0.44 g of phenol was weighed into a 100 ml volumetric flask. Approximately 95 ml of PBS was added to the flask to dissolve the phenol. The q.s. amount of PBS was added to the flask to dissolve the phenol. The resulting solution (4.4 mg/ml phenol) was used to prepare Solution B7.

Solution B7 Preparation

Solution B7 was prepared by weighing 2.5 mg of protamine sulfate into a 25 ml volumetric flask. Approximately 20 ml of phenol stock solution was added to the flask to dissolve the protamine sulfate. The q.s. amount of phenol stock solution was added to the flask. Solution B7 was filtered through a 0.22µ filter into a 50 ml glass vial. Solution B7 contained phenol 4.4 mg/ml and protamine base 0.075 mg/ml in PBS.

Aqueous Suspension 7

1.25 ml of solution A7 was pipetted into a 3.5 ml type I glass vial. The contents of the vial were stirred magnetically while 1.25 ml of solution B7 was pipetted into the vial. The vial was stoppered and sealed with an aluminum shell. The vial contents were stirred for 16 hours to allow suspension formation. Aqueous Suspension 7 contained insulinotropin 1 mg/ml, phenol 2.2 mg/ml, and protamine base 0.038 mg/ml in PBS. This suspension was used for in vivo pharmacokinetic studies in rats.

EXAMPLE 8

Insulinotropin (1 mg/ml) Suspension

Solution A12 Preparation 20 mg of insulinotropin was weighed into a 10 ml volumetric flask. Approximately 8 ml of PBS was added to the flask to disperse and dissolve the drug. The q.s. amount of PBS was added to the flask. Solution A12 was filtered by a syringe through a 0.22µ filter into a 10 ml glass vial. Solution A12 contained insulinotropin 2 mg/ml in PBS.

Solution B12

Solution B12 was prepared by weighing 20 mg of phenol into a 10 ml volumetric flask. Approximately 8 ml of PBS was added to the flask to dissolve the phenol. The q.s. amount of PBS was added to the flask. Solution B12 was filtered through a 0.22µ filter into a 10 ml glass vial. Solution B12 contained phenol 2 mg/ml in PBS.

Aqueous Suspension 12

4 ml of solution A12 was pipetted into a 10 ml type I glass vial. The contents of the vial were stirred while 4 ml of solution B12 was pipetted into the vial. The vial was stoppered and sealed with an aluminum shell. The vial contents were stirred for 16 hours to allow suspension formation. Aqueous Suspension 12 contained insulinotropin 1 mg/ml and phenol 1 mg/ml in PBS. This suspension was used for in vivo pharmacokinetic studies in rats.

EXAMPLE 9

Insulinotropin (1 mg/ml) Suspension

Solution A15 Preparation 20 mg of insulinotropin was weighed into a 10 ml volumetric flask. Approximately 8 ml of phosphate buffer (PB) was added to the flask to dissolve the drug. The q.s. amount of PB was added to the flask. Solution A15 was filtered by a syringe through a 0.22µ filter into a 10 ml glass vial. Solution A15 contained insulinotropin 2 mg/ml in PB.

Solution B15 Preparation

Solution B15 was prepared by weighing 8 mg of protamine sulfate into a 10 ml volumetric flask. Approximately 8 ml of PB was added to the flask to dissolve the protamine sulfate. The q.s. amount of PB was added to the flask. Solution B15 was filtered through a $0.22\mu$ filter into a 10 ml glass vial. Solution B15 contained protamine base 0.6 mg/ml in PBS.

Aqueous Suspension 15

3 ml of solution A15 was pipetted into a 10 ml type I glass vial. The contents of the vial were stirred while 3 ml of solution B15 was pipetted into the vial. The vial was stoppered and sealed with an aluminum shell. The vial contents were stirred for 16 hours to allow suspension formation. Aqueous Suspension 15 contained insulinotropin 1 mg/ml and protamine base 0.3 mg/ml in PB. This suspension was used for in vivo pharmacokinetic studies in rats.

EXAMPLE 10

Insulinotropin (1 mq/ml) Suspension

Solution A16 Preparation 20 mg of insulinotropin was weighed into a 10 ml volumetric flask. Approximately 8 ml of PB was added to the flask to dissolve the drug. The q.s. amount of PB was added to the flask. Solution A16 was filtered by a syringe through a $0.22\mu$ filter into a 10 ml glass vial. Solution A16 contained insulinotropin 2 mg/ml in PB.

Solution B16 Preparation

Solution B16 was prepared by weighing 44 mg of phenol into a 10 ml volumetric flask. Approximately 8 ml of PB was added to the flask to dissolve the phenol. The q.s. amount of PB was added to the flask. Solution B16 was filtered through a $0.22\mu$ filter into a 10 ml glass vial. Solution B16 contained phenol 4.4 mg/ml in PB.

Aqueous Suspension 16 bml of Solution A16 was pipetted into a 10 ml type I glass vial. The contents of the vial were stirred magnetically while 3 ml of Solution B16 was pipetted into the vial. The vial was stoppered and sealed with an aluminum shell. The vial contents were stirred for 16 hours to allow suspension formation. Aqueous Suspension 16 contained insulinotropin 1 mg/ml and phenol 2.2 mg in PB. This suspension was used for in vivo pharmacokinetic studies in rats.

EXAMPLE 11

Insulinotropin (1 mq/ml) Suspension

Aqueous Suspension 17

10 mg of insulinotropin was weighed into a 10 ml volumetric flask. Approximately 8 ml of PB was added to the flask to dissolve the drug. The q.s. amount of PB was added to the flask. The contents of the flask was filtered by syringe through a $0.22\mu$ filter into a 10 ml type I glass vial. The vial was stoppered and sealed with an aluminum shell. The vial contents were stirred for 16 hours to allow suspension formation. Aqueous Suspension 17 contained insulinotropin 1 mg/ml in PB. This suspension was used for in vivo pharmacokinetic studies in rats.

EXAMPLE 12

Insulinotropin (1 mg/ml) Suspension

Aqueous Suspension 18

10 mg of insulinotropin was weighed into a 10 ml volumetric flask. Approximately 8 ml of PBS was added to the flask to dissolve the drug. The q.s. amount of PBS was added to the flask. The contents of the flask were filtered by a syringe through a $0.22\mu$ filter into a 10 ml type I glass vial. The vial was stoppered and sealed with an aluminum shell. The vial contents were stirred gently (making sure no foam or bubble formed) for 16 hours to allow suspension formation. Aqueous Suspension 18 contained insulinotropin 1 mg/ml in PBS. This suspension was used for in vivo pharmacokinetic studies in rats.

EXAMPLE 13

Insulinotropin (0.2 mg/ml) Suspension

Solution A22 Preparation

Solution A22 was prepared by weighing 2 mg of insulinotropin into a 5 ml volumetric flask. Approximately 3 ml of PBS was added to the flask to dissolve the drug. The q.s. amount of PBS was added to the flask. Solution A22 was filtered by a syringe through a $0.22\mu$ filter into a 10 ml glass vial. Solution A22 contained insulinotropin 0.4 mg/ml in PBS.

Solution B22 Preparation

Solution B22 was prepared by weighing 44 mg of phenol into a 10 ml volumetric flask. Approximately 8 ml of PBS was added to the flask to dissolve the phenol. The q.s. amount of PBS was added to the flask. Solution B22 was filtered through a $0.22\mu$ filter into a 10 ml glass vial. Solution B22 contained phenol 4.4 mg/ml in PBS.

Aqueous Suspension 22

1.5 ml of solution A22 was pipetted into a 3.5 ml type I glass vial. The contents of the vial were stirred magnetically while 1.5 ml of solution B22 was pipetted into the vial. The vial was stoppered and sealed with an aluminum shell. The vial contents were stirred for 16 hours to allow suspension formation. Aqueous Suspension 22 contained insulinotropin 0.2 mg/ml and phenol 2.2 mg/ml in PBS. This suspension was used for in vivo pharmacokinetic studies in rats.

EXAMPLE 14

Insulinotropin (0.2 mg/ml) Suspension

Solution A23 Preparation

Solution A23 was prepared by weighing 2 mg of insulinotropin into a 5 ml volumetric flask. Approximately 3 ml of PBS was added to the flask to dissolve the drug. The q.s. amount of PBS was added to the flask. Solution A23 was filtered by a syringe through a $0.22\mu$ filter into a 10 ml glass vial. Solution A23 contained insulinotropin 0.4 mg/ml in PBS.

Solution B23 Preparation

Solution B23 was prepared by weighing 8.8 mg of phenol into a 10 ml volumetric flask. Approximately 8 ml of PBS was added to the flask to dissolve the phenol. The q.s. amount of PBS was added to the flask. Solution B23 was filtered through a $0.22\mu$ filter into a 10 ml glass vial. Solution B23 contained phenol 0.88 mg/ml in PBS.

Aqueous Suspension 23

1.5 ml of solution A23 was pipetted into a 3.5 ml type I glass vial. The contents of the vial were stirred magnetically while 1.5 ml of solution B23 was pipetted into the vial. The vial was stoppered and sealed with an aluminum shell. The vial contents were stirred for 16 hours to allow suspension formation. Aqueous Suspension 23 contained insulinotropin 0.2 mg/ml and phenol 0.44 mg/ml in PBS. This suspension was used for in vivo pharmacokinetic studies in rats.

EXAMPLE 15

Insulinotropin (1 mg/ml) Suspension

Solution A24 Preparation

Solution A24 was prepared by weighing 10 mg of insulinotropin into a 5 ml volumetric flask. Approximately 3 ml of PBS was added to the flask to dissolve the drug. The q.s. amount of PBS was added to the flask. Solution A24 was filtered by a syringe through a 0.22μ filter into a 10 ml glass vial. Solution A24 contained insulinotropin 2 mg/ml in PBS.

Solution B24 Preparation

Solution B24 was prepared by weighing 8 mg of protamine sulfate into a 10 ml volumetric flask. Approximately 8 ml of PBS was added to the flask to dissolve the protamine sulfate. The q.s. amount of PBS was added to the flask. Solution B24 was filtered through a 0.22μ filter into a 10 ml glass vial. Solution B24 contained protamine base 0.6 mg/ml in PBS.

Aqueous Suspension 24

1.5 ml of solution A24 was pipetted into a 3.5 ml type I glass vial. The contents of the vial were stirred magnetically while 1.5 ml of solution B24 was pipetted into the vial. The vial was stoppered and sealed with an aluminum shell. The vial contents were stirred for 16 hours to allow suspension formation. Aqueous Suspension 24 contained insulinotropin 1 mg/ml and protamine base 0.3 mg/ml in PBS. This suspension was used for in vivo pharmacokinetic studies in rats.

EXAMPLE 16

Insulinotropin (1 mg/ml) Suspension

Solution A25 Preparation

Solution A25 was prepared by weighing 10 mg of insulinotropin into a 5 ml volumetric flask. Approximately 3 ml of PBS was added to the flask to dissolve the drug. The q.s. amount of PBS was added to the flask. Solution A25 was filtered by a syringe through a 0.22μ filter into a 10 ml glass vial. Solution A25 contained insulinotropin 2 mg/ml in PBS.

Solution B25 Preparation

Solution B25 was prepared by weighing 53 mg of m-cresol into a 10 ml volumetric flask. Approximately 8 ml of PBS was added to the flask to dissolve the m-cresol. The q.s. amount of PBS was added to the flask. Solution B25 was filtered through a 0.22μ filter into a 10 ml glass vial. Solution B25 contained m-cresol 5.3 mg/ml in PBS.

Aqueous Suspension 25

1.5 ml of solution A25 was pipetted into a 3.5 ml type I glass vial. The contents of the vial were stirred magnetically while 1.5 ml of solution B25 was pipetted into the vial. The vial was stoppered and sealed with an aluminum shell. The vial contents were stirred for 16 hours to allow suspension formation. Aqueous Suspension 25 contained insulinotropin 1 mg/ml and m-cresol 2.5 mg/ml in PBS. This suspension was used for in vivo pharmacokinetic studies in rats.

EXAMPLE 17

Insulinotropin (0.5 mq/ml) Suspension

Solution A29 Preparation

Solution A29 was prepared by weighing 25 mg of insulinotropin into a 25 ml volumetric flask. Approximately 20 ml of PBS was added to the flask to dissolve the drug. The q.s. amount of PBS was added to the flask. Solution A29 was filtered by a syringe through a 0.22μ filter into a 50 ml glass vial. Solution A29 contained insulinotropin 1 mg/ml in PBS.

Solution B29 Preparation

Solution B29 was prepared by weighing 50 mg of phenol into a 50 ml volumetric flask. Approximately 40 ml of PBS was added to the flask to dissolve the phenol. The q.s. amount of PBS was added to the flask. Solution B29 was filtered through a 0.22μ filter into a 50 ml glass vial. Solution B29 contained phenol 1.0 mg/ml in PBS.

Aqueous Suspension 29

1.5 ml of solution A29 was pipetted into a 3.5 ml type I glass vial. The contents of the vial were stirred magnetically while 1.5 ml of solution B29 was pipetted into the vial. The vial was stoppered and sealed with an aluminum shell. The vial contents were stirred for 16 hours to allow suspension formation. Aqueous Suspension 29 contained insulinotropin 0.5 mg/ml and phenol 0.5 mg/ml in PBS. This suspension was used for in vivo pharmacokinetic studies in rats.

EXAMPLE 18

Insulinotropin (1 mg/ml) Suspension

Solution A31 Preparation 10 mg of insulinotropin was weighed into a 5 ml volumetric flask. Approximately 4 ml of PBS was added to the flask to disperse and dissolve the drug. The q.s. amount of PBS was added to the flask. Solution A31 was filtered by a syringe through a 0.22μ filter into a 10 ml glass vial. Solution A31 contained insulinotropin 2 mg/ml in PBS.

Solution B31 Preparation

Solution B31 was prepared by weighing 50 mg of phenol into a 50 ml volumetric flask. Approximately 40 ml of PBS was added to the flask to dissolve the phenol. The q.s. amount of PBS was added to the flask. Solution B31 was filtered through a 0.22μ filter into a 50 ml glass vial. Solution B31 contained phenol 1 mg/ml in PBS.

Aqueous Suspension 31

1.5 ml of solution A31 was pipetted into a 3.5 ml type I glass vial. The contents of the vial were stirred magnetically while 1.5 ml of solution B31 was pipetted into the vial. The vial was stoppered and sealed with an aluminum shell. The vial contents were stirred for 16 hours to allow suspension formation. Aqueous Suspension 31 contained insulinotropin 1 mg/ml and phenol 0.5 mg/ml in PBS. This suspension was used for in vivo pharmacokinetic studies in rats.

EXAMPLE 19

Insulinotropin (4 mq/mL) Suspension

Solution A51 Preparation 22.2 mg of insulinotropin was weighed into a 10 mL glass vial. 5 mL of PBS was pipetted into the vial to dissolve the drug. This solution was filtered through a 0.22μ filter (low protein binding) into a 10 mL glass vial. Solution A51 contained insulinotropin 4.44 mg/mL in PBS.

Solution B51 Preparation 110 mg of phenol and 30 mg of protamine sulfate were weighed into a 5 mL volumetric flask. Approximately 4 mL of PBS was added to the flask to dissolve the phenol and protamine sulfate. The flask was filled to the mark with FPBS. The solution was filtered through a 0.22μ filter (low protein binding) into a 10 mL glass vial. Solution B51 contained phenol 22 mg/mL and protamine base 4.5 mg/mL in PBS.

Aqueous Suspension 51

3 mL of Solution A51 and 0.33 mL of Solution B51 were pipetted into a 3.5 mL type I glass vial. The contents of the vial were shaken gently to ensure a homogeneous mix. The vial was allowed to sit at ambient temperature for 16 hours. Aqueous Suspension 51 contained insulinotropin 4 mg/mL, protamine base 0.44 mg/mL, and phenol 2.2 mg/mL in PBS. This suspension was used for in vivo pharmacokinetic studies in rats

EXAMPLE 20

Insulinotropin (4 mq/mL) Suspension

Solution A52 Preparation 22.2 mg of insulinotropin was weighed into a 10 mL glass vial. 5 mL of PBS was pipetted into the vial to dissolve the drug. This solution was filtered through a $0.22\mu$ filter (low protein binding) into a 10 mL glass vial. Solution A52 contained insulinotropin 4.44 mg/mL in PBS.

Solution B52 Preparation 110 mg of phenol and 15.6 mg of zinc acetate dihydrate were weighed into a 5 mL volumetric flask. Approximately 4 mL of water for injection was added to the flask to dissolve the phenol and zinc acetate dihydrate. The flask was filled to the mark with water for injection. The solution was filtered through a $0.22\mu$ filter (low protein binding) into a 10 mL glass vial. Solution B52 contained phenol 22 mg/mL and zinc acetate dihydrate 7.8 mg/mL in water for injection.

Aqueous Suspension 52

3 mL of Solution A52 and 0.33 mL of Solution B52 were pipetted into a 3.5 mL type I glass vial. The contents of the vial were shaken gently to ensure a homogeneous mix. The vial was allowed to sit at ambient temperature for 16 hours. Aqueous Suspension 52 contained insulinotropin 4 mg/mL, zinc acetate dihydrate 0.78 mg/mL, and phenol 2.2 mg/mL in PBS. This suspension was used for in vivo pharmacokinetic studies in rats.

EXAMPLE 21

Insulinotropin (4 mg/mL) Suspension

Phenol Solution Preparation 244 mg of phenol was weighed into a 100 mL volumetric flask. Approximately 90 mL of water for injection was added to the flask to dissolve the phenol. The flask was filled to the mark with water for injection. The pH of this solution was adjusted to pH 9.0 with 5% NaOH solution. The Phenol Solution contained phenol 2.44 mg/mL in water for injection pH 9.0.

Solution A71 Preparation 22.2 mg of insulinotropin was weighed into a 10 mL glass vial. 5 mL of the Phenol Solution was pipetted into the vial to dissolve the drug. This solution was filtered through a $0.22\mu$ filter (low protein binding) into a 10 mL glass vial. Solution A71 contained insulinotropin 4.44 mg/mL and phenol 2.44 mg/mL in water for injection.

Solution B71 Preparation 116 mg of protamine sulfate was weighed into a 10 mL volumetric flask. Approximately 8 mL of water for injection was added to the flask to dissolve the protamine sulfate. The flask was filled to the mark with water for injection. The solution was filtered through a $0.22\mu$ filter (low protein binding) into a 10 mL glass vial. Solution B71 contained protamine base 8.7 mg/mL in water for injection.

Solution C71 Preparation 156 mg of zinc acetate dihydrate and 1.632 g of NaCl were weighed into a 10 mL volumetric flask. Approximately 8 mL of water for injection was added to the flask to dissolve the zinc acetate dihydrate and NaCl. The flask was filled to the mark with water for injection. The solution was filtered through a $0.22\mu$ filter (low protein binding) into a 10 mL glass vial. Solution C71 contained zinc acetate dihydrate 15.6 mg/mL and NaCl 163.2 mg/mL in water for injection.

Aqueous Suspension 71

3 mL of Solution A71, 0.165 mL of Solution B71, and 0.165 mL of Solution C71 were pipetted into a 3.5 mL type I glass vial. The contents of the vial were shaken gently to ensure a homogeneous mix. The vial was allowed to sit at ambient temperature for 16 hours. Aqueous Suspension 71 contained insulinotropin 4 mg/mL, protamine base 0.435 mg/mL, zinc acetate dihydrate 0.78 mg/mL, NaCl 8.16 mg/mL, and phenol 2.2 mg/mL in water for injection. This suspension was used for in vivo pharmacokinetic studies in rats.

EXAMPLE 22

Insulinotropin (4 mg/mL) Suspension m-Cresol Solution Preparation 244 mg of m-cresol was weighed into a 100 mL volumetric flask. Approximately 90 mL of water for injection was added to the flask to dissolve the m-cresol. The flask was filled to the mark with water for injection. The pH of this solution was adjusted to pH 9.0 with 5% NaOH solution. The m-cresol Solution contained m-cresol 2.44 mg/mL in water for injection pH 9.0.

Solution A100 Preparation 22.2 mg of insulinotropin was weighed into a 10 mL glass vial. 5 mL of the m-cresol Solution was pipetted into the vial to dissolve the drug. This solution was filtered through a $0.22\mu$ filter (low protein binding) into a 10 mL glass vial. Solution A100 contained insulinotropin 4.44 mg/mL and m-cresol 2.44 mg/mL in water for injection.

Solution B100 Preparation 116 mg of protamine sulfate was weighed into a 10 mL volumetric flask. Approximately 8 mL of water for injection was added to the flask to dissolve the protamine sulfate. The flask was filled to the mark with water for injection. The solution was filtered through a $0.22\mu$ filter (low protein binding) into a 10 mL glass vial. Solution B100 contained protamine base 8.7 mg/mL in water for injection.

Solution C100 Preparation 156 mg of zinc acetate dihydrate and 1.632 g of NaCl were weighed into a 10 mL volumetric flask. Approximately 8 mL of water for injection was added to the flask to dissolve the zinc acetate dihydrate and NaCl. The flask was filled to the mark with water for injection. The solution was filtered through a $0.22\mu$ filter (low protein binding) into a 10 mL glass vial. Solution C100 contained zinc acetate dihydrate 15.6 mg/mL and NaCl 163.2 mg/mL in water for injection.

Aqueous Suspension 100

3 mL of Solution A100, 0.165 mL of Solution B100, and 0.165 mL of Solution C100 were pipetted into a 3.5 mL type I glass vial. The contents of the vial were shaken gently to ensure a homogeneous mix. The vial was allowed to sit at ambient temperature for 16 hours. Aqueous Suspension 100 contained insulinotropin 4 mg/mL, protamine base 0.435 mg/mL, zinc acetate dihydrate 0.78 mg/mL, NaCl 8.16 mg/mL, and m-cresol 2.2 mg/mL in water for injection. This suspension was used for in vivo pharmacokinetic studies in rats.

EXAMPLE 23

Insulinotropin (4 mg/mL) Suspension

Solution A68 Preparation 22.2 mg of insulinotropin was weighed into a 10 mL glass vial. 5 mL of the PBS as pipetted into the vial to dissolve the drug. This solution was filtered through a 0.22μ filter (low protein binding) into a 10 mL glass vial. Solution A68 contained insulinotropin 4.44 mg/mL in PBS.

Solution B68 Preparation 116 mg of protamine sulfate was weighed into a 10 mL volumetric flask. Approximately 8 mL of water for injection was added to the flask to dissolve the protamine sulfate, The flask was filled to the mark with water for injection. The solution was filtered through a 0.22μ filter (low protein binding) into a 10 mL glass vial. Solution B68 contained protamine base 8.7 mg/mL in water for injection.

Solution C68 Preparation 156 mg of zinc acetate dihydrate and 440 mg of phenol was weighed into a 10 mL volumetric flask. Approximately 8 mL of water for injection was added to the flask to dissolve the zinc acetate dihydrate and phenol. The flask was filled to the mark with water for injection. The solution was filtered through a 0.22μ filter (low protein binding) into a 10 mL glass vial. Solution C68 contained zinc acetate dihydrate 15.6 mg/mL and phenol 44 mg/mL in water for injection.

Aqueous Suspension 68

3 mL of Solution A68, 0.165 mL of Solution B68, and 0.165 mL of Solution C68 were pipetted into a 3.5 mL type I glass vial. The contents of the vial were shaken gently to ensure a homogeneous mix. The vial was allowed to sit at ambient temperature for 16 hours. Aqueous Suspension 68 contained insulinotropin 4 mg/mL, protamine base 0.435 mg/mL, zinc acetate dihydrate 0.78 mg/mL, and phenol 2.2 mg/mL in PBS. This suspension was used for in vivo pharmacokinetic studies in rats.

EXAMPLE 24

Insulinotropin (4 mq/mL) Suspension

Solution A67 Preparation 22.2 mg of insulinotropin was weighed into a 10 mL glass vial. 5 mL of the PBS was pipetted into the vial to dissolve the drug. This solution was filtered through a 0.22μ filter (low protein binding) into a 10 mL glass vial. Solution A67 contained insulinotropin 4.44 mg/mL in PBS.

Solution B67 Preparation 116 mg of protamine sulfate was weighed into a 10 mL volumetric flask. Approximately 8 mL of water for injection was added to the flask to dissolve the protamine sulfate. The flask was filled to the mark with water for injection. The solution was filtered through a 0.22μ filter (low protein binding) into a 10 mL glass vial. Solution B67 contained protamine base 8.7 mg/mL in water for injection.

Solution C67 Preparation 156 mg of zinc acetate dihydrate and 440 mg of m-cresol were weighed into a 10 mL volumetric flask. Approximately 8 mL of water for injection was added to the flask to dissolve the zinc acetate dihydrate and m-cresol. The flask was filled to the mark with water for injection. The solution was filtered through a 0.22μ filter (low protein binding) into a 10 mL glass vial. Solution C67 contained zinc acetate dihydrate 15.6 mg/mL and m-cresol 44 mg/mL in water for injection.

Aqueous Suspension 67

3 mL of Solution A67, 0.165 mL of Solution B67, and 0.165 mL of Solution C67 were pipetted into a 3.5 mL type I glass vial. The contents of the vial were shaken gently to ensure a homogeneous mix. The vial was allowed to sit at ambient temperature for 16 hours. Aqueous Suspension 67 contained insulinotropin 4 mg/mL, protamine base 0.435 mg/mL, zinc acetate dihydrate 0.78 mg/mL, and m-cresol 2.2 mg/mL in PBS. This suspension was used for in vivo pharmacokinetic studies in rats.

EXAMPLE 25

Solution A39 Preparation 67.6 mg of insulinotropin was weighed into a glass vial. Approximately 22 mL of water for injection was added to the vial to dissolve the insulinotropin. The pH of the vial content was adjusted to 9.6 using NaOH to make a clear solution. Water for injection was added to the vial to make the final drug concentration to be 2.5 mg/ml.

Solution B39 Preparation 386.8 mg of zinc acetate dihydrate was weighed into a 100 ml volumetric flask. Approximately 80 mL of water for injection was added to the flask to dissolve the zinc acetate dihydrate. The flask was filled to the mark with water for injection. Solution B39 contained zinc acetate dihydrate 3.9 mg/mL in water for injection.

Solution C39 Preparation 1.095 g of phenol was weighed into a 50 ml volumetric flask. Approximately 40 mL of water for injection was added to the flask to dissolve the phenol. The flask was filled to the mark with water for injection. Solution C39 contained phenol 21.9 mg/mL in water for injection.

Solution D39 Preparation 2.25 g of NaCl was weighed into a 25 mL volumetric flask. Approximately 20 mL of Solution C39 was added to the flask to dissolve the NaCl. The flask was filled to the mark with Solution C39. Solution D39 contained NaCl 9% (w/v) and phenol 21.9 mg/mL in water for injection.

Aqueous Suspension 39

All solutions were filtered through 0.22μ filters (low protein binding). 9 ml of Solution A39 was transferred to a 10 ml sample vial. 1 ml of Solution B39 was added to the vial while stirring gently. Precipitates were formed immediately. The pH was measured to be 7.0. The vial was allowed to sit at ambient temperature for about 18 hours. 4 ml of the sample was transferred to a separate 10 ml vial, and 0.44 ml of Solution D39 was added to the vial. The sample was stirred gently for 5 minutes and was then allowed to sit at ambient temperature overnight.

Aqueous Suspension 39 contained insulinotropin 2 mg/ml, phenol 2.2 mg/ml, NaCl 0.9%, and zinc acetate 0.39 mg/ml. This suspension was used for in vivo pharmacokinetic studies in rats.

EXAMPLE 26

Solution A53 Preparation 32.5 mg of insulinotropin was weighed into a 10 ml glass vial. 6 ml of water for injection was added to the vial. The pH of the vial content was adjusted to 9.6 using 1% (w/v) NaOH to make a clear solution. Appropriate amount of water for injection was added to make the drug concentration to be 5.0 mg/ml.

Solution B53 Preparation 390 mg of zinc acetate dihydrate was weighed into a 50 ml volumetric flask. Approximately 40 mL of water for injection was added to the flask to dissolve the zinc acetate dihydrate. The flask was filled to the mark with water for injection. Solution B53 contained zinc acetate dihydrate 7.8 mg/mL in water for injection.

Aqueous Suspension 53

All solutions were filtered through 0.22μ filters (low protein binding). 2.4 mL of Solution A53 was transferred to a 3.5 ml vial. 300 μl of Solution B53 was added to the vial while stirring gently. Birefringent precipitates were formed immediately after the addition. The pH was measured to be 6.8. After the vial was allowed to sit at ambient temperature for 20 hours, 7.5 μl of m-cresol was added directly to the supernatant of the settled suspension. The suspension was then stirred gently to dissolve the m-cresol. 300 μl of 9% NaCl solution was added to the suspension with stirring. Aqueous Suspension 53 contained insulinotropin 4 mg/mL, 0.9% NaCl, 0.78 mg/mL zinc acetate, and 2.5 mg/mL m-cresol in water for injection. This suspension was used for in vivo pharmacokinetic studies in rats.

EXAMPLE 27

Solution A54 Preparation 32.5 mg of insulinotropin was weighed into a 10 ml glass vial. 6 ml of water for injection was added to the vial. The pH of the vial content was adjusted to 9.6 using 1% (w/v) NaOH to make a clear solution. Appropriate amount of water for injection was added to make the drug concentration to be 5.0 mg/ml.

Solution B54 Preparation 390 mg of zinc acetate dihydrate was weighed into a 50 ml volumetric flask. Approximately 40 mL of water for injection was added to the flask to dissolve the zinc acetate dihydrate. The flask was filled to the mark with water for injection. Solution B54 contained zinc acetate dihydrate 7.8 mg/mL in water for injection.

Solution C54 Preparation 1.1 g of phenol and 4.5 g of NaCl were weighed into a 50 ml volumetric flask. Approximately 40 mL of water for injection was added to the flask. The flask was filled to the mark with water for injection. Solution C54 contained phenol 22 mg/mL and NaCl 90 mg/mL.

Aqueous Suspension 54

All solutions were filtered through 0.22μ filters (low protein binding). 2.4 ml of Solution A54 was transferred to a 3.5 ml vial. 300 μl of Solution B54 was added to the vial with stirring. Birefringent precipitates were formed immediately after the addition. The pH was measured to be 6.8. The sample was allowed to sit for 20 hours at ambient temperature. 300 μl of Solution C54 was added with gentle stirring. Aqueous Suspension 54 contained insulinotropin 4 mg/mL, zinc acetate dihydrate 0.78 mg/mL, phenol 2.2 mg/mL, and NaCl 9 mg/mL in water for injection. This suspension was used for in vivo pharmacokinetic studies in rats.

EXAMPLE 28

Solution A57 Preparation 15 mg of insulinotropin was weighed into a 10 mL glass vial. 3 mL of water for injection was added to the vial. The pH of the vial content was adjusted to 9.9 using 5% NaOH to dissolve the drug completely. Solution A57 contained insulinotropin 5.0 mg/mL in water for injection.

Solution B57 Preparation 780 mg of zinc acetate dihydrate was weighed into a 100 mL volumetric flask. Approximately 80 mL of water for injection was added to the flask to dissolve the zinc acetate dihydrate. The flask was filled to the mark with water for injection. Solution B57 contained zinc acetate dihydrate 7.8 mg/mL in water for injection.

Solution C57 Preparation 2.2 g of phenol and 9 g of NaCl were weighed into a 100 mL volumetric flask. Approximately 80 mL of water for injection was added to the flask to dissolve the phenol and the NaCl. The flask was filled to the mark with water for injection. Solution C57 contained phenol 22 mg/ml and NaCl 90 mg/mL in water for injection.

Aqueous Suspension 57

2.4 mL of Solution A57 was transferred to a 3.5 mL vial. The solution was stirred gently during addition of 300 μL of Solution B57. Precipitates were formed immediately after the addition of the Solution B57. The pH was measured and found to be 7.1. The sample was allowed to sit under ambient conditions for 24 hours. 300 μL of Solution C57 was added with gentle stirring. Aqueous Suspension 57 contained insulinotropin 4 mg/mL, zinc acetate dihydrate 0.78 mg/mL, phenol 2.2 mg/mL, and NaCl 9 mg/mL in water for injection. This suspension was used for in vivo pharmacokinetic studies in rats.

EXAMPLE 29

Solution A64 Preparation 53.3 mg of insulinotropin was weighed into a 30 mL glass vial. After adding 11 mL of water for injection, the pH of the vial contents was adjusted to 8.3 using 5% NaOH (w/v) to dissolve the insulinotropin. The pH was adjusted down to 6.0 using dilute HCl making sure that the solution still remained clear. Appropriate amount of water for injection was added to make the drug concentration to be 4.4 mg/ml. Solution A64 was filtered through a 0.22μ filter (low protein binding) into a 3.5 mL sample vial. 1.8 mL of the filtered solution was transferred to a separate sterile 3.5 mL vial, and the vial was allowed to sit at ambient temperature to crystallize for 3 days.

Solution B64 Preparation 780 mg of zinc acetate dihydrate was weighed into a 50 mL volumetric flask. Approximately 40 mL of water for injection was added to the flask to dissolve the zinc acetate dihydrate. The flask was filled to the mark with water for injection. Solution B64 contained zinc acetate dihydrate 15.6 mg/mL in water for injection.

Solution C64 Preparation 18 g of NaCl was weighed into a 100 mL volumetric flask. Approximately 80 mL of water for injection was added to the flask to dissolve the NaCl. The flask was filled to the mark with water for injection. Solution C64 contained NaCl 180 mg/mL in water for injection.

Aqueous Suspension 64

After crystallization was completed in Solution A64, 100 μL of Solution B64 was added to 1.8 mL of the crystal suspension was slow stirring. The sample was then allowed to sit at ambient temperature for 3 days. 100 μL of Solution C64 was added to the crystal suspension with gentle stirring. The pH of the suspension was adjusted to pH 7.3 using dilute NaOH. 5.0μ of m-cresol was added directly to the pH adjusted crystal suspension. Aqueous Suspension 64 contained insulinotropin 4 mg/mL, zinc acetate dihydrate 0.78 mg/mL, NaCl 9 mg/mL, and m-cresol 2.5 mg/mL in water for injection. This suspension was used for in vivo pharmacokinetic studies in rats.

EXAMPLE 30

Solution A69 Preparation 1 g of NaCl was weighed into a 100 mL volumetric flask. Approximately 80 mL of water for injection was added to the flask to dissolve the NaCl. The flask was filled to the mark with water for injection. Solution A69 contained NaCl 1% (w/v) in water for injection.

Solution B69 Preparation 390 mg of zinc acetate dihydrate was weighed into a 100 mL volumetric flask. Approximately 80 mL of water for injection was added to the flask to dissolve the zinc acetate dihydrate. The flask was filled to the mark with water for injection. Solution B69 contained zinc acetate dihydrate 3.9 mg/mL in water for injection.

Emulsion C69 Preparation 2.5 mL of sterile filtered (0.22$\mu$ low protein binding) m-cresol was transferred to a 100 mL volumetric flask. The flask was filled with water for injection to the mark and sonicated to produce a homogenous suspension. Emulsion C69 contained m-cresol 25 mg/mL in water for injection.

Aqueous Suspension 69

35.74 mg of insulinotropin was weighed into a 10 mL glass vial. 7 mL of Solution A69 was added. The pH of the vial contents was adjusted to 9.2 to dissolve the drug. The pH of the solution was re-adjusted to 6.5 using dilute HCl. Appropriate amount of water for injection was added to make the drug concentration to be 4.4 mg/ml. The solution was filtered through a 0.22$\mu$ filter (low protein binding). The solution was allowed to sit at ambient temperature for 6 days during which insulinotropin was crystallized. 1.5 mL of the crystal suspension was transferred to a separate vial. 167 $\mu$L of Solution B69 was added with gentle stirring. The sample was allowed to sit at ambient temperature for 1 day. 167 $\mu$L of emulsion C69 was added to the supernatant of the settled suspension. The sample was stirred to dissolve the m-cresol. Aqueous Suspension 69 contained insulinotropin 3.6 mg/ml, zinc acetate 0.36 mg/ml, NaCl 8.17 mg/ml and m-cresol 2.28 mg/ml in water for injection. This suspension was used for in vivo pharmacokinetic studies in rats.

EXAMPLE 31

Solution A101 Preparation 10 g of sodium acetate was weighed into a 100 ml volumetric flask. Approximately 80 mL of water for injection was added to the flask to dissolve the sodium acetate. The flask was filled to the mark with water for injection. Solution A200 contained 100 mg/ml sodium acetate in water for injection.

Aqueous Suspension 101

44.4 mg of insulinotropin was weighed into a 10 ml glass vial. 8 ml of water for injection was added to the flask. The pH of the vial contents was adjusted to 9.3 to obtain a clear solution. 1 mL of Solution A200 was added to the insulinotropin solution. The pH was then adjusted down to 6.5. The solution was filtered through a 0.22$\mu$ filter (low protein binding). The filtered solution was allowed to sit at ambient temperature for 3 days so that crystallization could occur. Aqueous Suspension 101 contained insulinotropin 4.9 mg/mL sodium acetate 11.1 mg/mL in water for injection. This suspension was used for in vivo pharmacokinetic study in rats.

EXAMPLE 32

Solution A82 Preparation 9 g of NaCl was weighed into a 100 mL volumetric flask. Approximately 80 mL of water for injection was added to the vial to dissolve the NaCl. The flask was filled to the mark with water for injection. Solution A82 contained NaCl 9% (w/v) in water for injection.

Solution B82 Preparation 789 mg of zinc acetate dihydrate was weighed into a 100 mL volumetric flask, Approximately 80 mL of water for injection was added to the vial to dissolve the zinc acetate dihydrate. The flask was filled to the mark with water for injection. Solution B82 contained zinc acetate dihydrate 7.89 mg/mL in water for injection.

Emulsion C82 Preparation 2.5 mL of sterile filtered (0.22$\mu$ low protein binding) m-cresol was transferred to a 100 mL volumetric flask. The flask was filled with water for injection to the mark and sonicated to produce a homogenous suspension. Emulsion C82 contained m-cresol 25 mg/mL in water for injection.

Aqueous Suspension 82

All solutions were filtered through 0.22$\mu$ filters (low protein binding). 45.34 mg of insulinotropin was added to a 10 ml vial to which 8 ml of water was added. The pH was adjusted to 9.3 using 5% NaOH. After 1 ml of Solution A82 was added to the vial, the pH of the solution was adjusted down to 6.55 using dilute HCl. The solution (5 mg/mL insulinotropin) was filtered through a 0.22$\mu$ filter (low protein binding). 81 $\mu$l of Aqueous Suspension 101 (see example 31) was added to the sterile filtered insulinotropin solution and dispersed by shaking the sample. The sample was then allowed to sit for 72 hours at ambient temperature to form a crystal suspension. 2.4 ml of the suspension was transferred to a 3.5 ml vial. 300 $\mu$l of Solution B82 was added to the vial with gentle stirring. The pH of the vial content was adjusted to 7.3 using dilute NaOH. 300 $\mu$l of Emulsion C82 was added to the supernatant of the settled suspension. Aqueous Suspension 82 contained insulinotropin 4 mg/ml, zinc acetate dihydrate 0.79 mg/mL, m-cresol 2.5 mg/mL and 0.9% NaCl in water for injection. This suspension was used for in vivo pharmacokinetic studies in rats.

EXAMPLE 33

GLP-1(7–36) Amide (1 mg/ml) Suspension

Solution A26 Preparation

Solution A26 was prepared by weighing 10 mg of GLP-1(7–36) Amide into a 5 ml volumetric flask. Approximately 3 ml of PBS was added to the flask to dissolve the drug. The q.s. amount of PBS was added to the flask. Solution A26 was filtered through a 0.22$\mu$ filter into a 10 ml glass vial. Solution A26 contained GLP-1(7–36) 2 mg/ml in PBS.

Solution B26 Preparation

Solution B26 was prepared by weighing 44 mg of phenol into eL 10 ml volumetric flask. Approximately 8 ml of PBS was added to the flask to dissolve the phenol. The q.s. amount of PBS was added to the flask. Solution 626 was filtered through a 0.22$\mu$ filter into a 10 ml glass vial. Solution B26 contained phenol 4.4 mg/ml in PBS.

Aqueous Suspension 26

1.5 ml of solution A26 was pipetted into a 3.5 ml type I glass vial. The contents of the vial were stirred magnetically while 1.5 ml of solution B26 was pipetted into the vial. The vial was stoppered and sealed with an aluminum shell. The vial contents were stirred gently (making sure no foam or bubble formed) for 18 hours to allow suspension formation. Aqueous Suspension 26 contained GLP-1(7–36) Amide 1 mg/ml and phenol 2.2 mg/ml in PBS. This suspension was used for in vivo pharmacokinetic studies in rats.

EXAMPLE 34

In one form of the invention, a low solubility form of GLP-1(7–37) is prepared by combining GLP-1(7–37) at from 2–15 mg/ml in buffer at pH 7–8.5 with a solution of a metal ion salt to obtain solutions with from 1–8 mg/ml GLP-1(7–37) at molar ratios of about 1:1 to 270:1 zinc to GLP-1(7–37). A heavy precipitate forms and is let stand overnight at room temperature. The solubility of GLP-1 (7–37) in the metal ion solution varies with the metal employed. Subsequent measurement of the solubility of the GLP-1(7–37) pellet in a non metal-containing solvent such as PBS or water shows that zinc, cobalt and nickel ions produce low solubility forms of GLP-1(7–37)

TABLE 1

Ability of Various metal ion salts to produce low solubility GLP-1 (7-37)

| Metal ion salt | Solubility in metal sol'n | Solubility in PBS |
| --- | --- | --- |
| Zn Acetate | 0.04 µg/ml | 0.04 µg/ml |
| Zn Chloride | 0.04 µg/ml | 0.03 µg/ml |
| Co Chloride | 0.11 µg/ml | 0.04 µg/ml |
| Ni Sulfate | 0.14 µg/ml | 0.07 µg/ml |
| Mn Chloride | 0.23 µg/ml | 1.64 µg/ml |
| Mg Chloride | 1.75 µg/ml | no ppt. |
| Ca Chloride | 1.98 µg/ml | no ppt. |

Note: In each case,100 µl of metal ion solution at 5 mM was added to 100 µl pGLP-1(7–37) at 5 mg/ml, mixed and allowed to stand overnight. The insoluble pellet was removed by centrifugation. The concentration of GLP-1 (7–37) remaining in the metal ion solution was measured. The pellet was resuspended in phosphate buffered saline (PBS), sonicated and allowed to stand overnight. Again insoluble material was pelleted and GLP-1(7–37) concentration measured.

EXAMPLE 35

Microcrystalline forms of GLP-1(7–37) can be obtained by mixing solutions of GLP-1(7–37) in buffer pH 7–8.5 with certain combinations of salts and low molecular weight polyethylene glycols (PEG). Table 2 describes six specific sets of conditions to produce microcrystalline forms of GLP-1(7–37).

TABLE 2

Selected Reagents Yielding Microcrystals

| Reagent# | Salt | Buffer | Precipitant |
| --- | --- | --- | --- |
| 1 | none | none | 0.4M K Na tartrate |
| 2 | 0.2M Na citrate | 0.1 M Tris pH 8.5 | 30% PEG 400 |
| 3 | 0.2M $MgCl_2$ | 0.1M HEPES pH 7.5 | 28% PEG 400 |
| 4 | 0.2M $MgCl_2$ | 0.1M HEPES pH 7.5 | 30% PEG 400 |
| 5 | 0.5 M $K_2HPO_4$ | none | 20% PEG 8000 |
| 6 | none | none | 30% PEG 1500 |

Note: GLP-1(7–37) stock at 5 mg/ml in 50mM Tris pH 8.1 was added 1:1 with reagent. Drops were viewed and scored for absence or presence of insoluble GLP-1(7–37) in crystalline or amorphous form. In general low mw PEG's appear to favor crystalline forms. Tris is tris(hydroxymethyl) aminomethane and HEPES is N-2-(Hydroxyethyl) piperazine-N-2-ethanesulfonic acid.

EXAMPLE 36

Specific combinations of GLP-1(7–37) and PEG concentrations are required to obtain microcrystalline forms and high yields. Table 3 shows specific combinations of PEG 600 and GLP-1(7–37) concentrations which produce microcrystalline as opposed to amorphous forms of the drug. The yield of GLP-1(7–37) in the insoluble form is shown also.

TABLE 3

Formation/yield of crystalline GLP-1 (7-37)

| GLP-1(7-37) | 15 PEG 600 | 22.5% PEG 600 | 30% PEG 600 |
| --- | --- | --- | --- |
| 2.0 mg/ml (Form/yield) | amorphous/8% | amorphous/10% | amorphous/8% |
| 3.5 mg/ml (Form/yield) | crystalline/62% | crystalline/26% | crystalline/59% |
| 5.0 mg/ml (Form/yield) | amorphous/34% | crystalline/63% | crystalline/72% |
| 6.5 mg/ml (Form/yield) | amorphous/52% | crystalline/76% | crystalline/82% |
| 8.0 mg/ml (Form/yield) | amorphous/55 | crystalline/82% | amorphous/66% |
| 9.5 mg/ml (Form/yield) | amorphous/69% | crystalline/85% | amorphous/83% |

Note: Microcrystals of GLP-1(7–37) are prepared by combining solutions of GLP-1(7–37) at 20 mg/ml in tris buffer at pH 8, 60% polyethylene glycol 600(PEG 600) in $H_2O$ and tris buffer pH 8 to obtain a final concentrations of from 15–30% PEG and from 3–10 mg/ml GLP-1. After standing overnight, microcrystals of GLP-1(7–37) form in the solution with yields from 50–85%.

EXAMPLE 37

This experiment exemplifies another form of the invention which involves treating preformed microcrystals of GLP-1(7–37) with various metal ions to produce low solubility microcrystalline forms. Microcrystals of GLP-1(7–37) prepared at 8 mg/ml GLP-1(7–37) and 22.5% PEG as described in Example 22 have a solubility equivalent to pure lyophilized GLP-1(7–37). In order to impart the desired property of low solubility for long-acting drug delivery, these preformed microcrystals can be treated with solutions of metal salts at ratios of metal:GLP-1(7–37) of from 1:1 to 260:1 overnight at room temp. The excess metal salt was removed by a centrifugation/washing process. Table 4 shows the results with several divalent cation metal salts as treatment.

TABLE 4

Solubility of GLP-1 (7-37) Crystals with Various Treatments

| Additive | GLP-1 (7-37) (mg/ml) in treatment sol'n | GLP-1 (7/37) (mg/ml) in PBS | GLP-1 (7-37) (mg/ml) in PBS/EDTA |
| --- | --- | --- | --- |
| None (PBS) | 1.2 | 1.2 | ND |
| Citrate pH 5.2 | 0.15 | ND | ND |
| $ZnCl_2$ pH 5.2 | 0.03 | 0.03 | 1.1 |
| ZnAc pH 5.2 | 0.01 | 0.02 | 1.1 |
| ZnAc pH 65 | 0.06 | 0.02 | 0.92 |
| $MgSO_4$ pH 5.2 | 0.50 | 0.55 | ND |
| $NiSO_4$ pH 5.2 | 0.10 | 0.04 | 0.45 |

TABLE 4-continued

Solubility of GLP-1 (7-37) Crystals with Various Treatments

| Additive | GLP-1 (7-37) (mg/ml) in treatment sol'n | GLP-1 (7/37) (mg/ml) in PBS | GLP-1 (7-37) (mg/ml) in PBS/EDTA |
|---|---|---|---|
| $MnCl_2$ pH 5.2 | 0.10 | 0.10 | ND |
| $CaCl_2$ pH 5.2 | 0.40 | 0.27 | ND |

Note: GLP-1(7–37) crystals are grown from a solution of 8 mg/ml IST in 50 mM Tris pH 8 with 22.5% PEG 600 added in $H_2O$. All additive treatment solutions are 100 mM divalent ion salt in 10 mM Na citrate pH 5.2 or Na MES pH 6.5.

EXAMPLE 38

Figure 8:
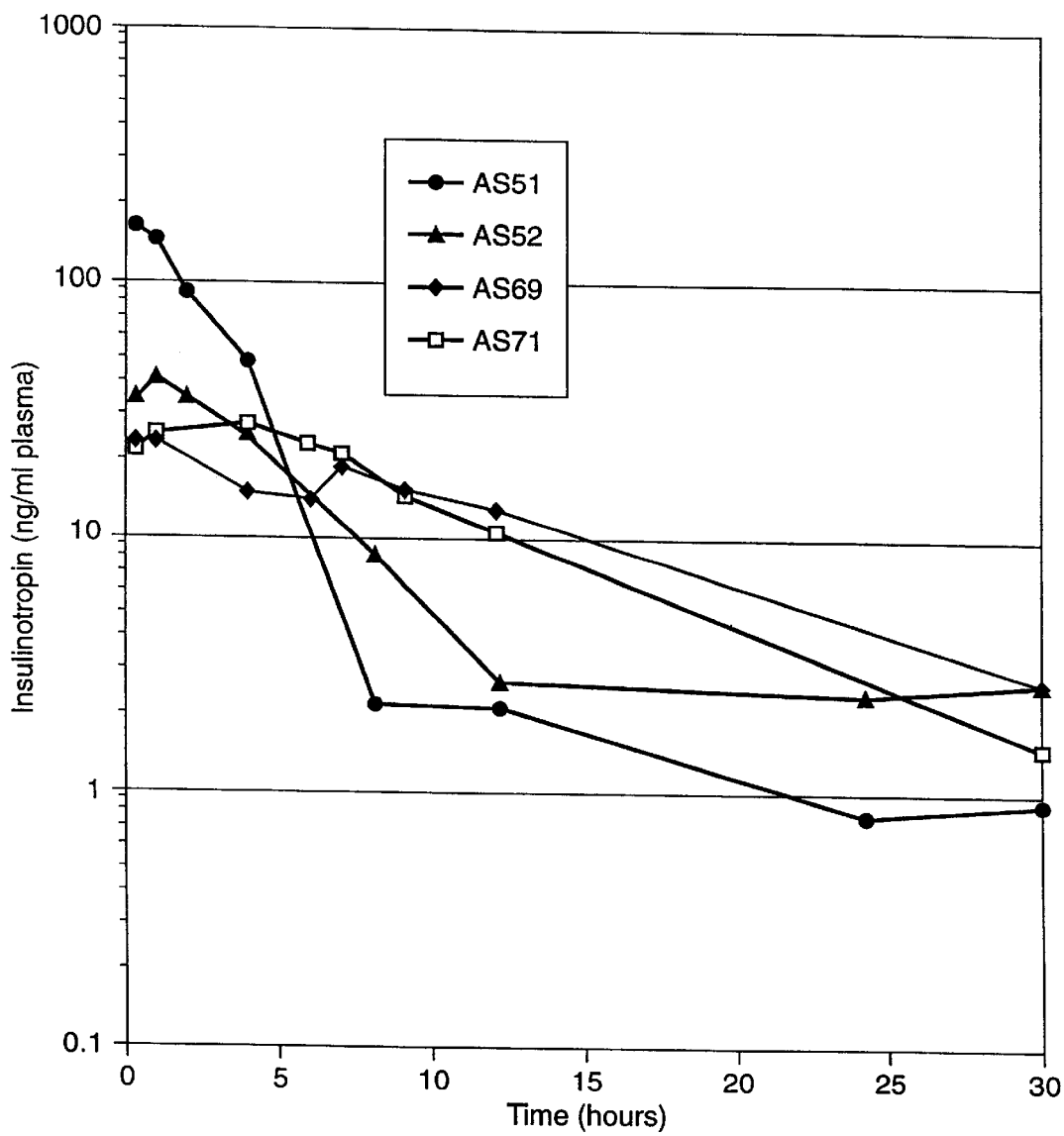
FIG. 8. Mean (n=3) Plasma Concentration of Insulinotropin in Rats After Subcutaneous Administration of Single 0.5 mg/0.13 ml Doses in Different Aqueous Suspensions (AS).
Figure 9:
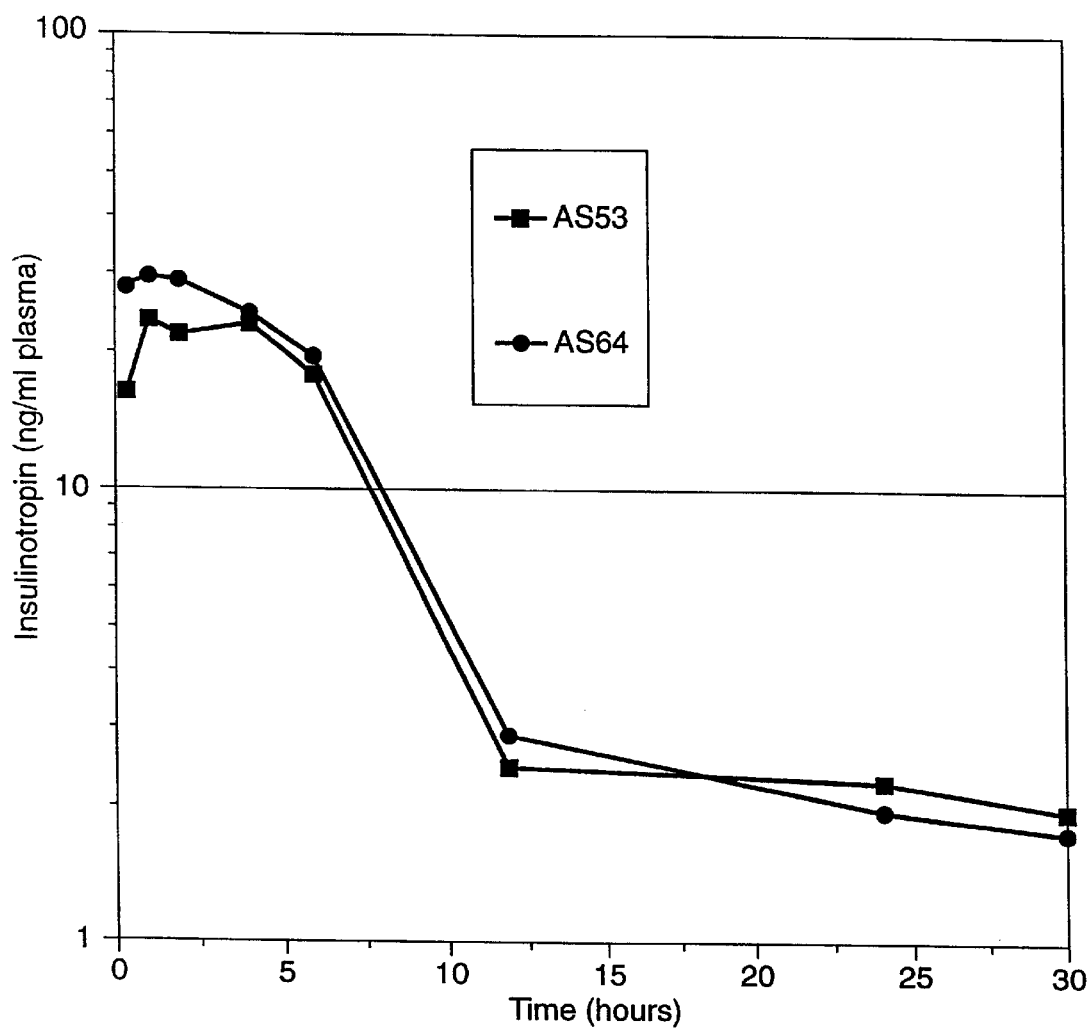
FIG. 9. Mean (n=3) Plasma Concentration of Insulinotropin in Rats After Subcutaneous Administration of Single 0.5 mg/0.13 ml Doses in Different Aqueous Suspensions (AS).
Figure 10:
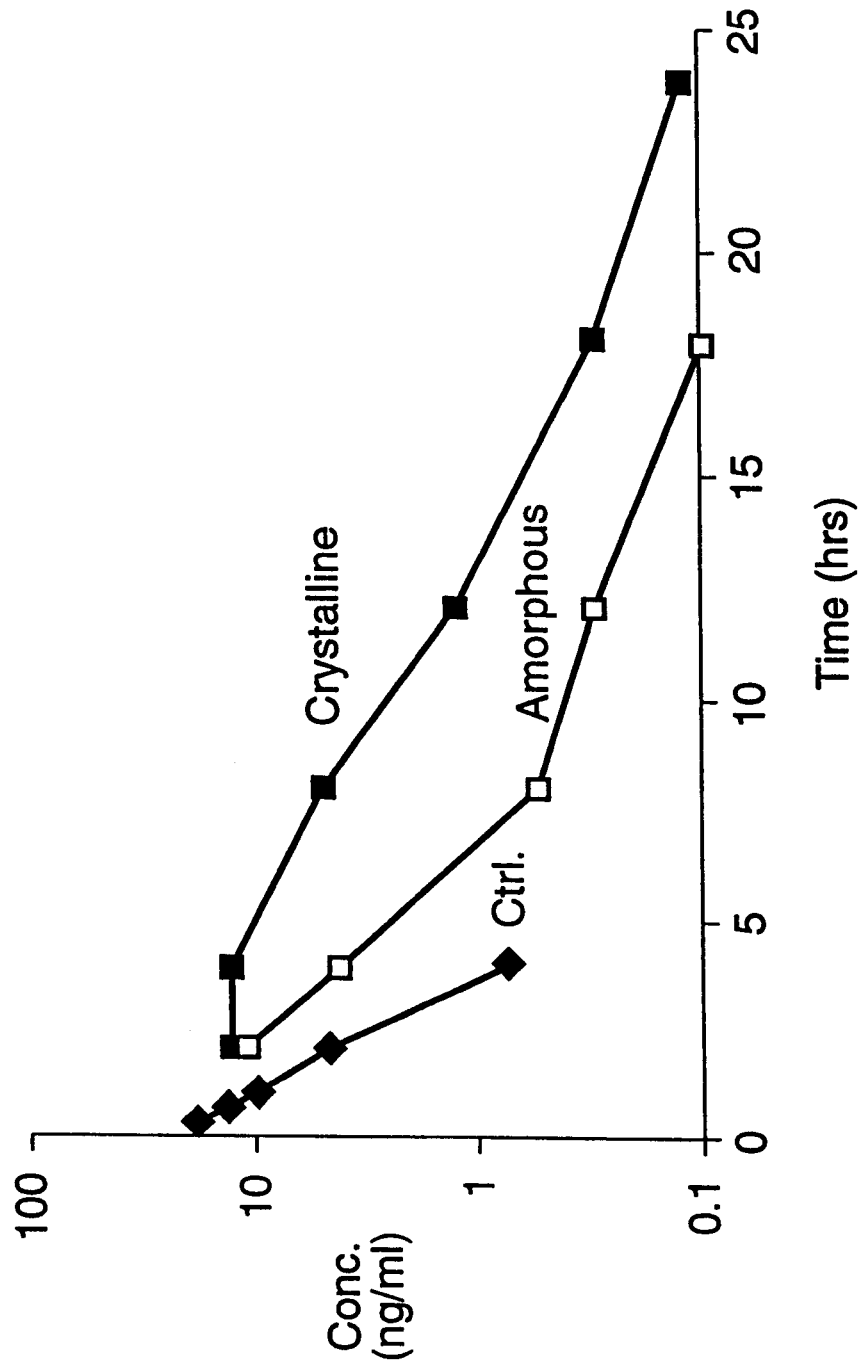
FIG. 10 shows pharmacokinetic studies of an insulinotropin zinc precipitate.

Using the methods described herein, both amorphous and microcrystalline low solubility formulations were prepared using zinc acetate. Subcutaneous injections were made in rats (three animals per formulation) and plasma levels of GLP-1(7–37) were measured by radioimmune assay over 24 hours. FIG. 8 shows the extended duration of the drug in plasma compared to a subcutaneous control injection of soluble GLP-1(7–37).

EXAMPLE 39

45% w/v Polyethylene Glycol 3350 (PEG)

1 mg/ml Insulinotropin 20 mM Phosphate Buffer qs Sterile Water for Injection (SWFI)

A 50% w/w PEG solution was prepared using SWFI. A 200 mM phosphate buffer was separately prepared with anhydrous sodium phosphate dibasic (26.85 mg/ml) and sodium phosphate monobasic monohydrate (1.41 mg/ml). If necessary, the pH of the buffer solution was brought to pH 8 with either sodium hydroxide or hydrochloric acid. The appropriate amount of insulinotropin was dissolved in enough of the buffer solution to make a 10 mg/ml solution of insulinotropin. The appropriate weight of the PEG solution was added to the insulinotropin solution, and a sufficient quantity of SWFI was used to bring the solution to the desired volume. The final solution was then sterile filtered with 0.2μ filter and aseptically filled into vials. The solution (0.5 ml) was injected subcutaneously in rats, and plasma insulinotropin levels followed by RIA assay.

EXAMPLE 40

1.32% w/v Hydroxyethyl Cellulose (HEC)

1 mg/ml Insulinotropin 20 mM Phosphate Buffer 100 mM Sodium Chloride qs Sterile Water For Injection (SWFI)

A 2% w/w hydroxethyl cellulose solution was prepared using SWFI. A 200 mM phosphate buffer was separately prepared with anhydrous sodium phosphate dibasic (26.85 mg/ml) and sodium phosphate monobasic monohydrate (1.41 mg/ml). If necessary, the pH of the buffer solution was brought to pH 8 with either sodium hydroxide or hydrochloric acid. The appropriate amount of insulinotropin and sodium chloride were dissolved in enough of the buffer solution to make a 10 mg/ml solution of insulinotropin. The appropriate weight of the HEC solution was added to the insulinotropin solution, and a sufficient quantity of SWFI was used to bring the solution to the desired volume. The final solution was then sterile filtered with a 0.2μ filter and aseptically filled into vials. The solution (0.5 ml) was injected subcutaneously in rats, and plasma insulinotropin followed by RIA assay.

EXAMPLE 41

18% w/v Pluronic F127

1 mg/ml Insulinotropin 20 mM Phosphate Buffer qs Sterile Water For Injection (SWFI)

A 20% W/W Pluronic F127 solution was prepared using SWFI. A Polytron (probe homogenizer) with an ice bath was used to dissolve the polymer. A 200 mM phosphate buffer was separately prepared with anhydrous sodium phosphate dibasic (26.85 mg/ml) and sodium phosphate monobasic monohydrate (1.41 mg/ml). If necessary, the pH of the buffer solution was brought to pH 8 with either sodium hydroxide or hydrochloric acid. The appropriate amount of insulinotropin was dissolve in enough of the buffer solution to make a 10 mg/ml solution of insulinotropin. The appropriate weight of the Pluronic solution was added to the insulinotropin solution, and a sufficient quantity of SWFI was used to bring the solution to the desired volume. The final solution was then sterile filtered with a 0.2 μm filter and aseptically filled into vials. The solution (0.5 ml) was injected subcutaneously in rats, and plasma insulinotropin levels followed by RIA assay.

EXAMPLE 42

Peanut Oil Suspension (Ball Milled)

1 mg/ml Insulinotropin

1 % Tween 80

Tween 80 was added at 1% level to peanut oil. This solution was sterile filtered with a 0.2 μm filter. Solid insulinotropin was then suspended in the oil. The particle size was reduced by ball milling with a Szesvari Attritor at 40 RPM for 18 hours (cold water jacket). This suspension was then filled into vials. The suspension (0.5 ml) was injected subcutaneously in rats, and plasma insulinotropin levels followed by RIA assay.

EXAMPLE 43

22.6% w/v Dextran 1 mg/ml Insulinotropin 20 mM Phosphate Buffer qs Sterile Water for Injection A 50% w/w Dextran solution was prepared using SWFI. A 200 mM phosphate buffer was separately prepared with anhydrous sodium phosphate dibasic (26.85 mg/ml) and sodium phosphate monobasic monohydrate (1.41 mg/ml). If necessary, the pH of the buffer solution was brought to pH 8 with either sodium hydroxide or hydrochloric acid. The appropriate amount of insulinotropin was dissolved in enough of the buffer solution to make 5.0 mg/ml solution of insulinotropin. The appropriate weight of the dextran solution was added to the insulinotropin solution, and a sufficient quantity of SWFI was used to bring the solution to the desired volume. The final solution was then sterile filtered with 0.2 μm filter and aseptically filled into vials. The solution (0.5 ml) was injected subcutaneously into rats, and plasma insulinotropin levels were followed by RIA assay.

EXAMPLE 44

Insulinotropin was crystallized from the mixture of phosphate buffered saline (PBS), ethanol, and m-cresol. A homogeneous insulinotropin slurry (10 mg/ml) was made with PBS in a glass vial, and a large volume of ethanol (9 times as much as the slurry) was added to the vial while the vial content was stirred magnetically. Very fine amorphous particles of insulinotropin formed. m-Cresol was added to the vial so that the resulting m-cresol concentration was 1% (v/v). The vial was capped to prevent solvent from evaporating. The crystallization mixture was stored at room temperature for a couple of days. Needle shape crystalline plates grew from the amorphous particles. The lengths of the crystals are between 50 and 200 µm, and widths between 2 and 4 µm.

EXAMPLE 45

Insulinotropin (1 to 4 mg/mL) was dissolved in 1% sodium sulfate (or sodium acetate, or sodium chloride, or ammonium sulfate) solution at higher pH values than 8, and the pH of the solution was lowered down to 6.0 to 7.5 with d-HCl. The clear solution was allowed to sit at ambient temperature. After a couple of days, needle or plate shape crystals were obtained depending on the crystallization conditions.

EXAMPLE 46

GLP-1(7–37) was dissolved in 50 mM glycine buffer containing 0.1 to 0.2 M NaCl at pH 8.5–9.5 at from 1 to 5 mg/ml. A solution of zinc salt (acetate or chloride) was added to obtain a molar ratio of from 0.5:1 to 1.5:1 zinc:GLP-1(7–37). Crystals of GLP-1(7–37) grew overnight at room temperature with yields from 70 to 97%.

EXAMPLE 47

GLP-1(7–37) crystals can be grown by vapor diffusion using the peptide dissolved in 100 mM Tris at pH 8–9.5 at from 10–20 mg/ml. The peptide solution is mixed 1:1 with the same buffer containing from 0.5 to 2.5 M NaCl then equilibrated in a sealed system against the full strength buffer (i.e. Tris with 0.5–2.5 M NaCl).

What is claimed is:

1. A composition of matter comprising:
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(E) Lys-Gly, and
(C) Lys-Gly-Arg;
(c) a polypeptide comprising the primary structure $H_2N—W—COOH$ wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed results in a peptide having insulinotropic activity;
(d) a peptide comprising the primary structure $H_2N—R—COOH$ wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
His-Ala-Glu-Gly-Thr-Phe-Trp-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide, and
(ii) a polymer selected from the group consisting of polyvinylalcohol, polyoxyethylene-polyoxypropylene copolymers, polysaccharides selected from the group consisting of cellulose, chitosan, acacia gum, karaya gum, guar gum, xanthan gum, tragacanth, alginic acid, carrageenan, agarose, and furcellarans, dextran, starch, starch derivatives, hyaluronic acid, polyamides, polyanhydrides, and polyortho esters; wherein said composition of matter is in an injectable formulation and comprises said compound of part (i) in crystalline or amorphous form having a solubility equal to or less than 500 µg/ml under physiological conditions; and wherein said composition of matter is capable of providing, in a patient who has been administered said composition by injection, plasma concentrations of said compound that are sufficient to enhance insulin action for the length of time necessary to achieve sustained glycemic control.

2. A method for the treatment of non-insulin dependent diabetes mellitus in a mammal in need of such treatment comprising the administration of a composition according to claim 1.

3. A composition of matter comprising:
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly, and
(C) Lys-Gly-Arg;
(c) a polypeptide comprising the primary structure $H_2N—W—COOH$ wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)

which polypeptide when processed in a mammal results in a peptide having insulinotropic activity;
  (d) a peptide comprising the primary structure

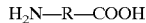

wherein R is an amino acid sequence selected from the group consisting of
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
  (e) a derivative of said peptides (a) through (d) wherein said derivative is selected from the group consisting of:
    (1) a pharmaceutically acceptable acid addition salt of said peptides;
    (2) a pharmaceutically acceptable carboxylate salt of said peptides;
    (3) a pharmaceutically acceptable alkali addition salt of said peptides;
    (4) a pharmaceutically acceptable lower alkyl ester of said peptides; and
    (5) a pharmaceutically acceptable amide of said peptides wherein said pharmaceutically acceptable amide is selected from the group consisting of amide, lower alkyl amide and lower dialkyl amide; and
  (ii) a pharmaceutically acceptable water-immiscible oil suspension; wherein said composition of matter is in an injectable formulation and comprises said compound of part (i) in particulate form having a solubility equal to or less than 500 μg/ml under physiological conditions; and wherein said composition of matter is capable of providing, in a patient who has been administered said composition by injection, plasma concentrations of said compound that are sufficient to enhance insulin action for the length of time necessary to achieve sustained glycemic control.

4. A composition according to claim 3 wherein said oil is selected from the group consisting of peanut oil, sesame oil, almond oil, castor oil, camellia oil, cotton seed oil, olive oil, corn oil, soy oil, safflower oil, coconut oil, and esters of fatty acids, esters of fatty alcohols.

5. A composition according to claim 3 further comprising a wetting agent.

6. A composition according to claim 5 wherein said wetting agent is a nonionic surfactant.

7. A composition according to claim 3 further comprising a suspending agent.

8. A method for the treatment of non-insulin dependent diabetes mellitus in a mammal in need of such treatment comprising of the administration of a composition according to claim 3.

9. A composition of matter in an injectable formulation comprising:
  (i) a compound selected from the group consisting of:
    (a) a peptide having the amino acid sequence:
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
    (b) a peptide having the amino acid sequence:
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
  wherein X is selected from the group consisting of:
    (A) Lys,
    (B) Lys-Gly, and
    (C) Lys-Gly-Arg;
    (c) a polypeptide comprising the primary structure

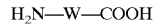

wherein W is an amino acid sequence selected from the group consisting of
  His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
  His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
  which polypeptide when processed in a mammal results in a peptide having insulinotropic activity;
    (d) a peptide comprising the primary structure

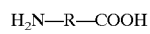

wherein R is an amino acid sequence selected from the group consisting of
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
    (e) a derivative of said peptides (a) through (d) wherein said derivative is selected from the group consisting of:
      (1) a pharmaceutically acceptable acid addition salt of said peptides;
      (2) a pharmaceutically acceptable carboxylate salt of said peptides;
      (3) a pharmaceutically acceptable alkali addition salt of said peptides;
      (4) a pharmaceutically acceptable lower alkyl ester of said peptides; and
      (5) a pharmaceutically acceptable amide of said peptides wherein said pharmaceutically acceptable amide is selected from the group consisting of amide, lower alkyl amide and lower dialkyl amide; and
  (ii) zinc (II) wherein said injectable composition of matter comprises said compound of part (i) in crystalline or amorphous form having a solubility equal to or less than 500 μg/ml under physiological conditions.

10. A composition according to claim 9 capable of achieving sustained glycemic control.

11. A composition according to claim 9 which is an aqueous suspension.

12. A method for the treatment of non-insulin dependent diabetes mellitus in a mammal in need of such treatment comprising of the administration of a composition according to claim 9.

13. A composition of matter in an injectable formulation comprising:
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly, and
(C) Lys-Gly-Arg;
(c) a polypeptide comprising the primary structure

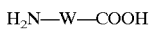

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed in a mammal results in a peptide having insulinotropic activity;
(d) a peptide comprising the primary structure

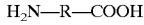

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide; and
(ii) a metal selected from the group consisting of Ni (II), Co (II), Mn (II), Fe (II), and Cu (II); wherein said injectable composition of matter comprises said compound of part (i) in crystalline or amorphous form having a solubility equal to or less than 500 µg/ml under physiological conditions.

14. A composition according to claim 13 capable of achieving sustained glycemic control.

15. A method for the treatment of non-insulin dependent diabetes mellitus in a mammal in need of such treatment comprising of the administration of a composition according to claim 13.

16. A composition of matter in an injectable formulation comprising:
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly, and
(C) Lys-Gly-Arg;
(c) a polypeptide comprising the primary structure

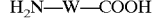

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed in a mammal results in a peptide having insulinotropic activity;
(d) a peptide comprising the primary structure

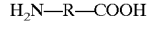

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;

(4) a pharmaceutically acceptable lower alkyl ester of said peptides; and (5) a pharmaceutically acceptable amide of said peptides wherein said pharmaceutically acceptable amide is selected from the group consisting of amide, lower alkyl amide and lower dialkyl amide; and (ii) a phenolic compound; wherein said injectable composition of matter comprises said compound of part (i) in precipitate or aggregate form having a solubility equal to or less than 500 µg/ml under physiological conditions, and wherein said composition of matter is capable of sustained glycemic control.

17. A composition according to claim 16 wherein said phenolic compound is selected from the group consisting of phenol, cresol, resorcinol, and methyl paraben.

18. A method for the treatment of non-insulin dependent diabetes mellitus in a mammal in need of such treatment comprising of the administration of a composition according to claim 16.

19. A composition of matter in an injectable formulation comprising:

(i) a compound selected from the group consisting of:

(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)

(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)

wherein X is selected from the group consisting of:
(A) Lys,
(B) Lys-Gly, and
(C) Lys-Gly-Arg;

(c) a Moypeptide comprising the primary structure

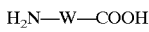

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Glu-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed in a mammal results in a peptide having insulinotropic activity;

(d) a peptide comprising the primary structure

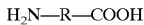

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Ser-Val-Lys; (SEQ ID NO:5) and (e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide; and (ii) a basic polypeptide and a phenolic compound, wherein said composition of matter comprises said compound of part (i) in precipitate or aggregate form having a solubility equal to or less than 500 µg/ml under physiological conditions; and wherein said composition of matter is capable of sustained glycemic control.

20. A method for the treatment of non-insulin dependent diabetes mellitus in a mammal in need of such treatment comprising of the administration of a composition according to claim 19.

21. A composition of matter in an injectable formulation comprising:

(i) a compound selected from the group consisting of:

(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)

(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)

wherein X is selected from the group consisting of:
(A) Lys,
(B) Lys-Gly, and
(C) Lys-Gly-Arg;

(c) a polypeptide comprising the primary structure

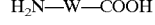

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed in a mammal results in a peptide having insulinotropic activity;

(d) a peptide comprising the primary structure

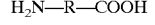

wherein R is an amino acid sequence selected from the group consisting of

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Thr-Leu-Val-Lys; (SEQ ID NO:5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide; and
(ii) a basic polypeptide, a phenolic compound, and a metal ion; wherein said injectable composition of matter comprises said compound of part (i) in precipitate or aggregate form having a solubility equal to or less than 500 µg/ml under physiological conditions; and wherein said composition of matter is capable of sustained glycemic control.

22. A composition according to claim 21 wherein said basic polypeptide is protamine.

23. A composition according to claim 21 wherein said metal ion is zinc.

24. A method for the treatment of non-insulin dependent diabetes mellitus in a mammal in need of such treatment comprising of the administration of a composition according to claim 21.

25. A composition of matter in an injectable formulation comprising:
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly, and
(C) Lys-Gly-Arg;
(c) a polypeptide comprising the primary structure

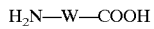

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed in a mammal results in a peptide having insulinotropic activity;
(d) a peptide comprising the primary structure

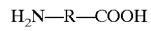

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide; and
(ii) a pharmaceutically acceptable medium;
wherein said peptides and derivatives thereof have been subjected to conditions resulting in amorphous or crystalline material formation, and wherein said injectable composition of matter comprises said compound of part (i) in amorphous or crystalline form having a solubility equal to or less than 500 µg/ml under physiological conditions.

26. A composition according to claim 25 wherein said conditions are high shear, exposure to salts; or combinations thereof.

27. A composition according to claim 26 wherein said salt is selected from the group consisting of ammonium sulfate, sodium sulfate, lithium sulfate, lithium chloride, sodium citrate, ammonium citrate, sodium phosphate, potassium phosphate, sodium chloride, potassium chloride, ammonium chloride, sodium acetate, ammonium acetate, magnesium sulfate, calcium chloride, ammonium nitrate, and sodium formate; and combinations thereof.

28. A method for the treatment of non-insulin dependent diabetes mellitus in a mammal in need of such treatment comprising of the administration of a composition according to claim 25.

29. A composition of matter in an injectable formulation comprising:
(i) a compound selected from the group consisting of:
(a) a peptide having the amino acid sequence:

His-Ala-Glu-Gly-Thr-Phe-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) lays,
(B) Lys-Gly, and
(C) Lys-Gly-Arg;
(c) a polypeptide comprising the primary structure

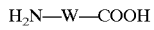

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed in a mammal results in a peptide having insulinotropic activity;
(d) a peptide comprising the primary structure

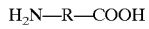

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:4)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide; and
(ii) zinc (II) and a phenolic compound; wherein said injectable composition of matter comprises said compound of part (i) in crystalline or amorphous form having a solubility equal to or less than 500 µg/ml under physiological conditions.
30. A composition according to claim 29 capable of achieving sustained glycemic control.

31. A composition according to claim 29 which is an aqueous suspension.
32. A composition of matter in an injectable formulation comprising:
(i) a compound selected from the group consisting of:
(a) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQUENCE ID NO: 2)
(b) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQUENCE ID NO: 7)
wherein X is selected from the group consisting of:
(A) Lys,
(B) Lys-Gly, and
(C) Lys-Gly-Arg;
(c) a polypeptide comprising the primary structure

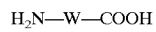

wherein W is an amino acid sequence selected from the group consisting of
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQUENCE ID NO: 1) and
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQUENCE ID NO: 6)
which polypeptide when processed in a mammal results in a peptide having insulinotropic activity;
(d) a peptide comprising the primary structure

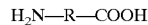

wherein R is an amino acid sequence selected from the group consisting of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly; (SEQ ID NO:2)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg; (SEQ ID NO:3)
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly; (SEQ ID NO:4) and
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys; (SEQ ID NO:5) and
(e) a derivative of said peptides (a) through (d) wherein said derivative is selected from the group consisting of:
(1) a pharmaceutically acceptable acid addition salt of said peptides;
(2) a pharmaceutically acceptable carboxylate salt of said peptides;
(3) a pharmaceutically acceptable alkali addition salt of said peptides;
(4) a pharmaceutically acceptable lower alkyl ester of said peptides; and
(5) a pharmaceutically acceptable amide of said peptides wherein said pharmaceutically acceptable amide is selected from the group consisting of amide, lower alkyl amide and lower dialkyl amide; and (ii) zinc (II) and a basic polypeptide; wherein said injectable composition of matter comprises said compound of part (i) in crystalline or amorphous form having a solubility equal to or less than 500 μg/ml under physiological conditions.

33. A composition according to claim 32 capable of achieving sustained glycemic control.

34. A composition according to claim 32 which is an aqueous suspension.

35. A composition according to claim 32 wherein the basic polypeptide is protamine.

36. The method of any one of claims 2, 8, 12, 15 or 18, 20, 24 or wherein said administration is subcutaneous.

37. The method of any one of claims 2, 8, 12, 15 or 18, 20, 24 or 28 wherein said administration is intramuscular.

* * * * *

UNITED STATES PATENT AND TRADEMARK OFFICE
CERTIFICATE OF CORRECTION

PATENT NO. : 6,284,727 B1
DATED : September 4, 2001
INVENTOR(S) : Kim et al.

Page 1 of 1

It is certified that error appears in the above-identified patent and that said Letters Patent is hereby corrected as shown below:

<u>Column 60,</u>
Claim 36, "claims 2, 8, 12, 15 or 18, 20, 24 or" was deleted and -- claims 2, 8, 12, 15, 18, 20, 24 or 28 -- was inserted.
Claim 37, "claims 2, 8, 12, 15 or 18, 20, 24 or 28" was deleted and -- claims 2, 8, 12, 15, 18, 20, 24 or 28 -- was inserted.

Signed and Sealed this

Fourteenth Day of May, 2002

*Attest:*

JAMES E. ROGAN
*Attesting Officer*     *Director of the United States Patent and Trademark Office*